(12) United States Patent
Ludovici et al.

(10) Patent No.: US 7,563,781 B2
(45) Date of Patent: Jul. 21, 2009

(54) TRIAZOLOPYRIMIDINE DERIVATIVES

(75) Inventors: Donald W. Ludovici, Quakertown, PA (US); Richard W. Connors, Harleysville, PA (US); Steven J. Coats, Quakertown, PA (US); Li Liu, Doylestown, PA (US); Bart L. De Corte, Southampton, PA (US); Dana L. Johnson, Upper Black Eddy, PA (US); Mark J. Schulz, Skippack, PA (US)

(73) Assignee: Janssen Pharmaceutica NV (BE)

( * ) Notice: Subject to any disclaimer, the term of this patent is extended or adjusted under 35 U.S.C. 154(b) by 104 days.

(21) Appl. No.: 11/329,642

(22) Filed: Jan. 11, 2006

(65) Prior Publication Data

US 2007/0015207 A1   Jan. 18, 2007

(51) Int. Cl.
  C07D 487/04   (2006.01)
  C07F 9/40   (2006.01)
  A61K 31/5355   (2006.01)
  A61K 31/519   (2006.01)
  C07D 239/30   (2006.01)
  A61P 35/00   (2006.01)
  G01N 33/53   (2006.01)
  C07H 21/04   (2006.01)
  C12P 21/06   (2006.01)
  C12N 5/06   (2006.01)
  C07K 16/40   (2006.01)
  C12N 9/12   (2006.01)

(52) U.S. Cl. .................. 514/81; 514/261.1; 514/234.2; 514/252.12; 544/118; 544/244; 544/254; 544/326; 544/329; 435/7.1; 435/69.1; 435/194; 435/348; 536/23.2; 530/391.1

(58) Field of Classification Search .............. 514/261.1, 514/234.5, 234.2, 81, 252.12; 544/254, 244, 544/118
See application file for complete search history.

(56) References Cited

U.S. PATENT DOCUMENTS 6,716,831 B1   4/2004   Breault et al.

FOREIGN PATENT DOCUMENTS

| JP | 59062594 A | * | 4/1984 |
| WO | WO 97/12971 A1 | | 4/1997 |
| WO | WO 2004018473 | * | 3/2004 |
| WO | WO 2004/043953 A1 | | 5/2004 |
| WO | WO 2005012304 | * | 7/2004 |
| WO | WO 2005012307 | * | 7/2004 |
| WO | WO 2005/012304 A2 | | 2/2005 |
| WO | WO 2005/012307 A1 | | 2/2005 |

OTHER PUBLICATIONS

Partial International Search Report re: PCT/US2006/000999 dated Mar. 22, 2007.
International Search Report re: PCT/US2006/000999 dated Jun. 29, 2007.
International Preliminary Report on Patentability re: PCT/US2006/000999 dated Jul. 17, 2007.
Expert Opin. Ther. Patents (2003) 13(6): 925-927.
Expert Opin. Pharmacother. (2003) 4(2): 227-234.
Fisher, R.P., et al 'A Novel Cyclin Associates with M015/CDK7 to Form the CDK-Activating Kinase' Cell (1994) vol. 78, No. 4 pp. 713-724.
Larochelle, S. et al 'T-Loop Phosphorylation Stabilizes the CDK7-cyclin H-MAT1 Complex In Vivo and Regulates its CTD Kinase Activity' The Embo Journal (2001) vol. 20, No. 14 pp. 3749-3759.
Lawrie, A.M., et al 'Xenopus Phospho-CDK7/cyclin H Expressed in Baculoviral-Infected Insect Cells' Protein Expression and Purification (2001) vol. 23, No. 2 pp. 252-260.
Makela, T.P., et al 'A Cyclin Associated with the CDK-Activating Kinase M015' Nature (1994) vol. 371, No. 6494 pp. 254-257.
Patent Abstracts of Japan vol. 008, No. 162, Jul. 26, 1984 (corresponds to JP 59062594).
Rossignol, M., et al 'Substrate Specificity of the CDK-Activating Kinase (CAK) is Altered Upon Association with TFIIH' The Embo Journal (1997) vol. 16, No. 7 pp. 1628-1637.
Sandrock, B., et al 'A Yeast Four-Hybrid System Identifies CDK-Activating Kinase as a Regulator of the XPD Helicase, a Subunit of Transcription Factor IIH' The Journal of Biological Chemistry (2001) vol. 276, No. 38 pp. 35328-35333.
Tassan, J.P. et al Cell Cycle Analysis of the Activity, Subcellular Localization, and Subunit Composition of Human CAK (CDK-Activating Kinase) The Journal of Cell Biology (1994) vol. 127, No. 2 pp. 467-478.

* cited by examiner

*Primary Examiner*—Mark L Berch
*Assistant Examiner*—Cecilia M Jaisle

(57) ABSTRACT

The invention relates to the discovery of triazolopyrimidine derivatives of formula (I), which have been found to exhibit inhibitory activity against the serine-tyrosine and tyrosine kinases.

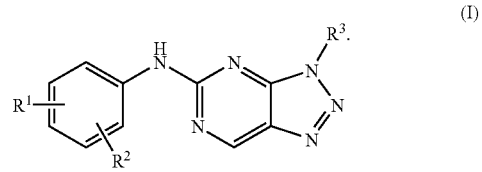

2 Claims, 1 Drawing Sheet

TRIAZOLOPYRIMIDINE DERIVATIVES

BACKGROUND

Cells proliferate by means of traversing a series of discreet steps encompassing the cell cycle. This cycle, composed of G1, S, G2 and M phases, is regulated by a complex network of cell cycle checkpoints that assure events that are required for the next phase are completed before that phase begins. In part these checkpoints are regulated by phosphorylation of regulatory proteins such as Rb (Retinoblastoma protein) and p53. The phosphorylation of these key regulatory proteins is mediated in part by a class of Serine-Threonine protein kinases termed Cyclin Dependent Kinases (Cdks). Regulation of the activity of these Cdks is found to be aberrant in many human cancers and other proliferative disorders.

Regulation, in turn, of the activity of the cdks is a complex series of phosphorylation, dephosphorylation and protein-protein interactions that result in an active cdk complex, which can phosphorylate substrate proteins. One phosphorylation event that is required for the activation of cdks is mediated by Cyclin Dependent Kinase Activating Kinase (CAK). CAK phosphorylates a Threonine residue in the T-loop of all cdks such as cdk1, cdk2, and cdk4. This phosphorylation allows the cyclin subunit and ATP to bind to the cdk subunit. It is believed that inhibition of this required event will inhibit the activity of cdks and disrupt the ability of human cancer cells to traverse the cell cycle and proliferate.

In an analogous fashion, cells contain systems that allow chemical communication between the external environment and internal signaling pathways. Focal Adhesion Kinase (FAK) is a trans membrane protein that receives signals from the integrin class of cell adhesion molecules and transmits the signal to intracellular pathways regulating cell proliferation, cell motility and protection from cell death (Apoptosis). FAK is a tyrosine kinase in which the major phosphorylation site is tyr 397 of the FAK itself. This autophosphorylation event stimulates SH2 mediated interations of numerous proteins, thereby amplifying the FAK signaling pathway. Overexpression of FAK and the associated tyrosine kinase activity has been well documented in human tumors and correlates well with the severity of disease. Therefore, an inhibitor of FAK may have value as an anti-cancer agent.

The invention is based on the discovery that certain compounds inhibit the Serine-Threonine kinase activity of CAK and other kinases and also inhibit the Tyrosine kinase activity of FAK and thus possess anti-cancer activity.

It is also believed that inhibition of focal adhesion kinase (FAK), which is involved in signal transduction pathways, induces apoptosis (cell-death) and/or inhibits cell migration. Therefore, an inhibitor of FAK may have value as an anti-cancer agent.

The invention is based on the discovery that certain compounds surprisingly inhibit the effects of cell cycle kinases showing selectivity for cdk2, cdk4, and cdk6, and also inhibit FAK and thus possess anti-cancer activity.

SUMMARY OF THE INVENTION

The invention relates to the discovery of triazolopyrimidine derivatives of formula I which have been found to exhibit inhibitory activity against the tyrosine kinases and serine-theonine kinases.

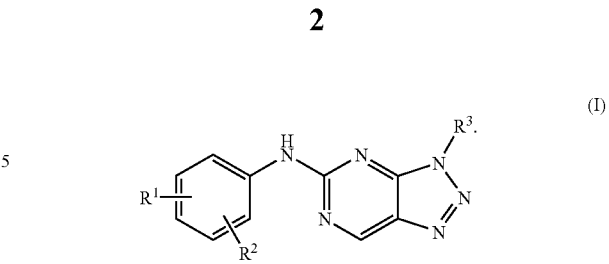

Compounds of the invention have been found to inhibit kinase activities associated with various forms of cancer and metastasis such as CAK and other kinases and FAK.

DETAILED DESCRIPTION

The invention is directed to a compound of Formula (I)

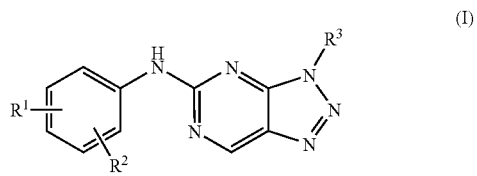

wherein:

$R^1$ is $C_{1-8}$alkyl optionally substituted with one to three substituents independently selected from the group consisting of $NR^aR^b$, —P(═O)(O$C_{1-6}$alkyl)$_2$, and $C_{1-6}$alkoxycarbonyl; $C_{2-8}$alkenyl; $C_{2-8}$alkynyl, wherein $C_{2-8}$alkenyl and $C_{2-8}$alkynyl is each optionally substituted with a substituent selected from the group consisting of aryl and $C_{1-6}$alkoxycarbonyl; $C_{1-8}$alkoxy optionally substituted with one to three substituents independently selected from the group consisting of hydroxy and $NR^aR^b$; —C(═O)$NR^aR^b$; $C_{1-6}$alkoxycarbonyl wherein $C_{1-6}$alkoxy is optionally substituted with one to three substituents independently selected from the group consisting of hydroxy and $NR^aR^b$; aminocarbonyl; $C_{1-6}$alkylaminocarbonyl; di($C_{1-6}$alkyl)amino-carbonyl; aryl; heteroaryl selected from tetrazolyl, thiadiazolyl, oxazolyl, and pyrimidinyl, optionally substituted with one to three $C_{1-6}$alkyl substituents; —S(O)$_{1-2}NR^cR^d$; or when $R^1$ and $R^2$ are attached to adjacent carbon atoms, $R^1$ and $R^2$ can together form a benzofused $C_{3-7}$cycloalkyl, benzofused heterocyclyl, or benzofused heteroaryl;

$R^a$ and $R^b$ is each independently hydrogen, $C_{1-6}$alkyl, or $C_{3-7}$cycloalkyl; wherein $C_{1-6}$alkyl and $C_{3-7}$cycloalkyl is each optionally substituted with one to three substituents independently selected from the group consisting of $NR^cR^d$, hydroxy, $C_{1-6}$alkoxycarbonyl, carboxy, aryl, and heteroaryl selected from tetrazolyl, thiadiazolyl, oxazolyl, and pyrimidinyl, wherein heteroaryl is optionally substituted with one to three $C_{1-6}$alkyl substituents; or $R^a$ and $R^b$ taken together with the nitrogen atom to which they are both attached form a monocyclic heterocycle optionally containing one to three additional heteroatoms selected from the group consisting of O, S, and N; and wherein said heterocycle is optionally substituted with one to three substituents independently selected from the group consisting of $C_{1-6}$alkyl, $C_{1-6}$alkoxy, aryl($C_{1-6}$)alkyl, $C_{1-6}$alkoxycarbonyl, carboxy, oxo, and hydroxy;

$R^c$ and $R^d$ is each a independently hydrogen or $C_{1-6}$alkyl; or $R^c$ and $R^d$ taken together with the nitrogen atom to which they are both attached form a 5-8 membered monocyclic heterocycle, wherein said heterocycle is optionally substituted with one to three substituents selected from the group consisting of $C_{1-6}$alkyl, $C_{1-6}$alkoxy, aryl($C_{1-6}$)alkyl, $C_{1-6}$alkoxycarbonyl, carboxy, oxo, and hydroxy;

$R^2$ is one to three substituents independently selected from the group consisting of hydrogen, $C_{1-6}$alkyl, $C_{1-6}$alkoxy, $C_{3-7}$cycloalkyl, hydroxy, amino, $C_{1-6}$alkylamino, and di($C_{1-6}$alkyl)amino;

$R^3$ is a substituent selected from the group consisting of aryl($C_{1-6}$)alkyl, aryl, $C_{3-7}$cycloalkyl, benzofused-$C_{3-7}$cycloalkyl, quinolinyl, benzothiazolyl, benzoimidazolyl, pyrazolyl, and fluorenyl;

wherein any aryl-containing substituent of $R^3$ is optionally substituted with one to three substituents independently selected from the group consisting of $C_{1-6}$alkyl, $C_{2-6}$alkenyl, $C_{2-6}$alkynyl, $C_{1-6}$alkoxy, hydroxy, cyano, fluoro, carboxyl, $C_{3-7}$cycloalkyl, —NR$^a$R$^b$, —C(=O)NR$^a$R$^b$, $C_{1-6}$alkoxycarbonyl, —S(O)$_{1-2}$NR$^c$R$^d$, and a heteroaryl selected from pyrimidinyl, thiadiazoloyl, tetrazolyl, pyrazolyl, and oxazolyl;

and wherein $C_{3-7}$cycloalkyl or any alkyl-containing substituent of $R^3$ is optionally substituted with one to three substituents independently selected from the group consisting of hydroxy, —NR$^a$R$^b$, —C(=O)NR$^a$R$^b$, $C_{1-6}$alkoxycarbonyl, carboxy, —S(O)$_{1-2}$NR$^c$R$^d$, and —S(O)$_{1-2}$C$_{1-6}$alkyl;

or a pharmaceutically acceptable salt thereof.

The invention is also directed to a compound of formula (I)

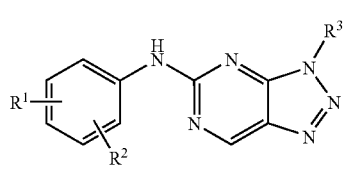

(I)

wherein:

$R^1$ is a substituent selected from the group consisting of $C_{1-8}$alkyl optionally substituted with one to three substituents independently selected from the group consisting of NR$^a$R$^b$, and —P(=O)(OC$_{1-6}$alkyl)$_2$; $C_{2-8}$alkenyl; and $C_{2-8}$alkynyl wherein $C_{2-8}$alkenyl and $C_{2-8}$alkynyl is each optionally substituted with aryl; $C_{1-8}$alkoxy substituted with at least two substituents independently selected from the group consisting of hydroxy and —NR$^a$R$^b$; —C(=O)NR$^a$R$^b$ provided that $R^3$ is a benzofused cycloalkyl, quinolinyl, benzothiazolyl, or benzoimidazolyl attached via the non-benzo portion of the ring system; $C_{1-6}$alkoxycarbonyl wherein $C_{1-6}$alkoxy is substituted with one to three substituents independently selected from the group consisting of hydroxy and —NR$^a$R$^b$; aryl; heteroaryl selected from tetrazolyl, thiadiazolyl, oxazolyl, and pyrimidinyl, provided that $R^3$ is a benzofused cycloalkyl, quinolinyl, benzothiazolyl, or benzoimidazolyl attached via the non-benzo portion of the ring system; wherein said aryl and the heteroaryl substituents of $R^3$ are optionally substituted with one to three $C_{1-6}$alkyl substituents; or when $R^1$ and $R^2$ are attached to adjacent carbon atoms, $R^1$ and $R^2$ can together form a benzofused $C_{3-7}$cycloalkyl, benzofused heterocyclyl, or benzofused heteroaryl;

$R^a$ and $R^b$ is each independently hydrogen, $C_{1-6}$alkyl, or $C_{3-7}$cycloalkyl; wherein $C_{1-6}$alkyl and $C_{3-7}$cycloalkyl is each optionally substituted with one to three substituents independently selected from the group consisting of hydroxy, $C_{1-6}$alkoxycarbonyl, carboxy, aryl, and heteroaryl selected from tetrazolyl, thiadiazolyl, oxazolyl, and pyrimidinyl, wherein heteroaryl is optionally substituted with one to three $C_{1-6}$alkyl substituents; or R$^a$ and R$^b$ taken together with the nitrogen atom to which they are both attached form a monocyclic heterocycle optionally containing one to three additional heteroatoms selected from the group consisting of O, S, and N; and wherein said heterocycle is optionally substituted with one to three substituents independently selected from the group consisting of $C_{1-6}$alkyl, $C_{1-6}$alkoxy, aryl($C_{1-6}$)alkyl, $C_{1-6}$alkoxycarbonyl, carboxy, oxo, and hydroxy;

R$^c$ and R$^d$ is each independently hydrogen or $C_{1-6}$alkyl; or R$^c$ and R$^d$ taken together with the nitrogen atom to which they are both attached form a 5-8 membered monocyclic heterocycle, wherein said heterocycle is optionally substituted with one to three substituents selected from the group consisting of $C_{1-6}$alkyl, $C_{1-6}$alkoxy, aryl($C_{1-6}$)alkyl, $C_{1-6}$alkoxycarbonyl, carboxy, oxo, and hydroxy;

$R^2$ is one to three substituents independently selected from the group consisting of hydrogen, $C_{1-6}$alkyl, $C_{1-6}$alkoxy, $C_{3-7}$cycloalkyl, hydroxy, amino, $C_{1-6}$alkylamino, and di($C_{1-6}$alkyl)amino;

$R^3$ is a substituent selected from the group consisting of aryl($C_{1-6}$)alkyl, aryl, $C_{3-7}$cycloalkyl, benzofused-$C_{3-7}$cycloalkyl, quinolinyl, benzothiazolyl, benzoimidazolyl, pyrazolyl, and fluorenyl;

wherein any aryl-containing substituent of $R^3$ is optionally substituted with one to three substituents independently selected from the group consisting of $C_{1-6}$alkyl, $C_{2-6}$alkenyl, $C_{2-6}$alkynyl, $C_{1-6}$alkoxy, hydroxy, cyano, fluoro, carboxyl, $C_{3-7}$cycloalkyl, —NR$^a$R$^b$, —C(=O)NR$^a$R$^b$, $C_{1-6}$alkoxycarbonyl, —S(O)$_{1-2}$NR$^c$R$^d$, and a heteroaryl selected from pyrimidinyl, thiadiazoloyl, tetrazolyl, pyrazolyl, and oxazolyl;

and wherein $C_{3-7}$cycloalkyl or any alkyl-containing substituent of $R^3$ is optionally substituted with one to three substituents independently selected from the group consisting of hydroxy, NR$^a$R$^b$, C(=O)NR$^a$R$^b$, $C_{1-6}$alkoxycarbonyl, carboxy, —S(O)$_{1-2}$NR$^c$R$^d$, and —S(O)$_{12}$C$_{1-6}$alkyl;

or a pharmaceutically acceptable salt thereof.

The invention relates to triazolopyrimidine derivatives which possess cell-cycle inhibitory activity and are useful for their anti-cancer activity and are useful in methods of treatment of mammals, especially humans. The invention also relates to processes for the manufacture of said compounds, to pharmaceutical compositions containing them, and to their use in the manufacture of medicaments of use in the production of an anti-cell-proliferation effect in a warm-blooded animal such as man.

The compounds of the invention are useful as pharmaceutical agents for kinase-related diseases, particularly those involving inappropriate stimulation of CAK and other kinases and FAK. Especially relevant uses are the inhibition of cancers such as papillary renal and hepatocellular carcinomas, prostate and colorectal cancers, osteosarcomas, tumor metastases such as those originating from head and neck squamous cell carcinomas, or other disease states in which etiology is due to or results in excessive cellular proliferation. Compounds of the invention may additionally be useful for the treatment of tumor related angiogenesis.

The compounds of the invention are effective cell cycle inhibitors, i.e., they are anti-cell proliferation agents. The compounds are also effective inhibitors of FAK. Accordingly, the compounds of the invention are useful in the treatment of diseases or medical conditions mediated alone or in part by cdk and/or FAK enzymes, i.e. the compounds may be used to produce a cdk inhibitory effect in a warm-blooded animal in need of such treatment. Thus, the compounds of the invention provide a method for treating the proliferation and/or migration of malignant cells characterised by inhibition of cdk and/or FAK enzymes, i.e. the compounds may be used to produce an anti-proliferative/migration effect mediated alone or in part by the inhibition of cdks and/or FAK. The compounds are also useful as FAK inhibitors by inducing cell-death (apoptosis).

The compounds possesses a wide range of anti-cancer properties, since cdks and/or FAK have been implicated in many common human cancers such as leukemia and breast, lung, colon, rectal, stomach, prostate, bladder, pancreas, and ovarian cancer. The compounds of the invention possess activity against a range of leukemias, lymphoid malignancies, and solid tumors such as carcinomas and sarcomas in tissues such as the liver, kidney, prostate, and pancreas. Compounds of the invention are expected to slow the growth of primary and recurrent solid tumors of, for example, the colon, breast, prostate, lungs, and skin. More particularly, such compounds inhibit the growth of those primary and recurrent solid tumors which are associated with cdks and/or FAK, especially those tumors which are significantly dependent on cdks and/or FAK for their growth and spread, including for example, certain tumors of the colon, breast, prostate, lung, vulva, and skin.

The compounds of the invention are expected to be of value in the treatment of disease states associated with aberrant cell cycles and cell proliferation such as fibroproliferative and differentiative disorders, psoriasis, rheumatoid arthritis, Kaposi's sarcoma, haemangioma, acute and chronic nephropathies, atheroma, atherosclerosis, arterial restenosis, autoimmune diseases, acute and chronic inflammation, bone diseases, and ocular diseases with retinal vessel proliferation.

One embodiment of the invention is a compound for use as a medicament; and the use of a compound in the manufacture of a medicament for use in the production of an anti-cancer, cell cycle inhibitory (anti-cell-proliferation) effect and/or FAK inhibitory (anti-cell migration and/or apoptosis inducing) effect in a warm-blooded animal such as man. Particularly, a cell cycle inhibitory effect is produced at the G1-S phase boundary by inhibition of cdk2, cdk4, and/or cdk6, whereas a G2/M boundary arrest may be mediated by inhibiotopn of cdk1 and cdk2. Since CAK activity is required for the actiovity of all cdks it is anticipated that CAK inhibitors would produce cell cycle arrest at all checkpoints.

A general aspect of the invention is a method of inhibiting the activity of one or more kinases selected from the group consisting of a CAK, a FAK, and other kinases in a cell, comprising the step of administering a compound of the invention to the cell.

An embodiment of the invention is a method for producing an anti-cancer, cell cycle inhibitory (anti-cell-proliferation) effect and/or FAK inhibitory (anti-cell migration and/or apoptosis inducing) effect in a warm-blooded animal, such as man, in need of such treatment which comprises administering to said animal an effective amount of a compound of the invention.

The size of the dose required for a therapeutic or prophylactic treatment of a particular disease will necessarily be varied depending on the host treated, the route of administration, and the severity of the illness being treated. A unit dose in the range, for example, 1-100 mg/kg, preferably 1-50 mg/kg is envisaged.

In addition to a compound of the invention, one or more other substances and/or treatments may be used. Such joint treatment may be achieved by way of the simultaneous, sequential, or separate administration of the individual components of the treatment. In the field of oncology it is normal practice to use a combination of different forms of treatment. The other component(s) of such joint treatment may be surgery, radiotherapy, or chemotherapy. Such chemotherapy may cover three main categories of therapeutic agent:

(i) other cell cycle inhibitory agents that work by the same or different mechanisms from those defined herein;

(ii) cytostatic agents such as antioestrogens (for example, tamoxifen, toremifene, raloxifene, droloxifene, and iodoxyfene), progestogens (for example, megestrol acetate), aromatase inhibitors (for example, anastrozole, letrazole, vorazole, and exemestane), antiprogestogens, antiandrogens (for example, flutamide, nilutamide, bicalutamide, and cyproterone acetate), LHRH agonists and antagonists (for example, goserelin acetate and luprolide), inhibitors of testosterone 5α-dihydroreductase (for example, finasteride), anti-invasion agents (for example, metalloproteinase inhibitors such as marimastat and inhibitors of urokinase plasminogen activator receptor function), and inhibitors of growth factor function (such growth factors include for example platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example, antifolates like methotrexate, fluoropyrimidines such as 5-fluorouracil, purine and adenosine analogues, cytosine arabinoside); antitumor antibiotics (for example, anthracyclines such as doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincrisitine and taxoids like taxol, taxotere); topoisomerase inhibitors (for example epipodophyllotoxins like etoposide and teniposide, amsacrine, topotecan). Thus, an embodiment of the invention is a pharmaceutical product comprising a compound of the invention and an additional anti-tumor substance for the joint treatment of cancer. An anti-emetic may also be usefully administered, when using such joint treatment.

One embodiment of the invention is a method of inhibiting cell cycle kinases or focal adhesion kinases in a subject, which comprises the step of administering to the subject a therapeutically effective amount a compound of the formula (I), or an optical isomer, enantiomer, diastereomer, racemate, racemic mixture, ester, prodrug form, or pharmaceutically acceptable salt thereof.

The term "subject" refers to an animal, preferably a mammal, most preferably a human, who is the object of treatment.

The term "therapeutically effective amount" means that amount of active compound or pharmaceutical agent that elicits the biological or medicinal response is being sought, which includes prevention or alleviation of the symptoms of the disease or disorder being treated.

The term "prophylactically effective amount" means that amount of a pharmaceutical drug that will prevent or reduce the risk of occurrence of the biological or medical event that is sought to be prevented in an animal or human.

The term "pharmaceutically acceptable salts" means non-toxic salts of the compounds employed in this invention which are generally prepared by reacting the free acid with a suitable organic or inorganic base. Examples of such salts include acetate, benzenesulfonate, benzoate, bicarbonate, bisulfate, bitartrate, borate, bromide, calcium, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, mrethylbromide, methylnitrate, methylsulfate, mucate, napsylate, nitrate, oleate, oxalate, pamaote, palmitate, panthothenate, phosphate/diphosphate, polygalacturonate, potassium, salicylate, sodium, stearate, subacetate, succinate, tannate, tartrate, teoclate, tosylate, triethiodide, and valerate salts.

Methods are known in the art for determining therapeutically and prophylactically effective doses for the instant pharmaceutical composition. For example, the compound can be employed at a daily dose in the range of about 100 mg to 400 mg, usually on a regimen of 1 to 2 times per day, for an average adult human. The effective amount, however, may be varied depending upon the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The compound may be administered to a subject by any conventional route of administration, including, intravenous, oral, subcutaneous, intramuscular, intradermal, and parenteral. Depending on the route of administration, compounds of formula (I) can be constituted into any form. For example, forms suitable for oral administration include solid forms, such as pills, gelcaps, tablets, caplets, capsules (each including immediate release, timed release and sustained release formulations), granules, and powders. Forms suitable for oral administration also include liquid forms, such as solutions, syrups, elixirs, emulsions, and suspensions. In addition, forms useful for parenteral administration include sterile solutions, emulsions, and suspensions.

To prepare the pharmaceutical compositions of the invention, one or more compounds of formula (I) or salt thereof as the active ingredient is intimately admixed with a pharmaceutical carrier according to conventional pharmaceutical compounding techniques. Carriers are necessary and inert pharmaceutical excipients, including, but not limited to, binders, suspending agents, lubricants, flavorants, sweeteners, preservatives, dyes, and coatings. In preparing compositions in oral dosage form, any of the usual pharmaceutical carriers may be employed. For example, for liquid oral preparations, suitable carriers and additives include water, glycols, oils, alcohols, flavoring agents, preservatives, coloring agents and the like; for solid oral preparations, suitable carriers and additives include starches, sugars, diluents, granulating agents, lubricants, binders, disintegrating agents and the like. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed.

Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carrier. The tablets or pills can be coated or otherwise compounded to provide a dosage form affording the advantage of prolonged action. For example, the tablet or pills can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The active drug can also be administered in the form of liposome delivery systems, such as small unilamellar vesicles, large unilamellar vesicles and multilamellar vesicles. Liposomes can be formed from a variety of phospholipids, such as cholesterol, stearylamine, or phosphatidylcholines.

Active drug may also be delivered by the use of monoclonal antibodies as individual carriers to which the compound molecules are coupled. Active drug may also be coupled with soluble polymers as targetable drug carriers. Such polymers can include polyvinyl-pyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, active drug may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates, and cross linked or amphipathic block copolymers of hydrogels.

Preferably these compositions are in unit dosage forms such as tablets, pills, capsules, powders, granules, sterile parenteral solutions or suspensions, metered aerosol or liquid sprays, drops, ampoules, auto-injector devices or suppositories, for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection.

The pharmaceutical compositions herein will contain, per dosage unit, e.g., tablet, capsule, powder, injection, teaspoonful, suppository and the like, an amount of the active ingredient necessary to deliver an effective dose as described above. For example, the pharmaceutical compositions herein can contain, per unit dosage unit, from about 25 to about 200 mg of the active ingredient. Preferably, the range is from about 50 to about 150 mg of the active ingredient.

When any variable (e.g., aryl, heterocyclyl, $R^1$, $R^2$, etc.) occurs more than once in a substituent list, its definition on each occurrence is independent of any other occurrence.

Bond lines drawn into a ring system from a substituent variable indicate that the substituent may be attached to any of the substitutable ring atoms.

As used herein, the following terms are intended to have the following definitions.

"Alkyl" means a saturated aliphatic branched or straight-chain monovalent hydrocarbon radical substituent or alkyldiyl linking group having a specified number of carbon atoms, wherein the radical substituent is derived by the removal of one hydrogen atom from a carbon atom and the alkyldiyl linking group is derived by the removal of one hydrogen atom from each of two carbon atoms in the chain. The term "$C_{1-8}$alkyl" means a radical having from 1-8 carbon atoms in a linear or branched arrangement. "$C_{1-6}$alkyl" includes methyl, ethyl, propyl, butyl, pentyl, and hexyl. Alkyl and alkyldiyl radicals may be attached to a core molecule via a terminal carbon atom or via a carbon atom within the chain. Similarly, substituent variables may be attached to an alkyl or alkyldiyl radical when allowed by available valences.

"Alkoxy" means an alkyl radical attached through an oxygen linking atom. "$C_{1-4}$alkoxy" includes the radicals methoxy, ethoxy, propoxy, and butoxy. An alkoxy radical may be attached to a core molecule and further substituted where indicated.

"Aryl" means an aromatic monocyclic or polycyclic ring system radical. Aryl ring systems include phenyl, naphthalenyl, fluorenyl, indenyl, azulenyl, and anthracenyl.

"Hetero," when used as a prefix for a ring system, refers to the replacement of at least one carbon atom member in the ring system with a heteroatom selected from N, S, or O.

In general, IUPAC nomenclature rules are used herein.

Pharmaceutical Preparations and Methods of Use

Pharmaceutical compositions of the invention may, alternatively or in addition to a compound of formula (I), comprise a pharmaceutically acceptable salt of a compound of formula (I) or a prodrug or pharmaceutically active metabolite of such a compound or salt in admixture with a pharmaceutically acceptable carrier. The term "composition" therefore means a product comprising at least a compound of the invention and a pharmaceutically acceptable carrier or any such alternatives to a compound of the invention and a pharmaceutically acceptable carrier, as well as any product which results, directly or indirectly, from such combinations.

Certain compounds of formula (I) may exist in various stereoisomeric or tautomeric forms. The invention encompasses all such active compounds, including active compounds in the form of essentially pure enantiomers, racemic mixtures, and tautomers.

The compounds of the invention may be present in the form of pharmaceutically acceptable salts. For use in medicines, the salts of the compounds of this invention refer to non-toxic "pharmaceutically acceptable salts." FDA-approved pharmaceutically acceptable salt forms include pharmaceutically acceptable acidic/anionic or basic/cationic salts.

Pharmaceutically acceptable acidic/anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methyinitrate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate, and triethiodide salts.

The compounds of the invention include pharmaceutically acceptable anionic salt forms, wherein the anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate, and triethiodide salts.

The anionic salt form of a compound of the invention includes an anionic salt selected from the acetate, bromide, camsylate, chloride, edisylate, fumarate, hydrobromide, hydrochloride, iodide, isethionate, lactate, mesylate, napsylate, salicylate, sulfate, and tosylate salts.

During any of the processes for preparation of the compounds of the invention, it may be necessary and/or desirable to protect sensitive or reactive groups on any of the molecules concerned. This may be achieved by means of conventional protecting groups, such as those described in *Protective Grours in Organic Chemistry*, ed. J. F. W. McOmie, Plenum Press, 1973; and T. W. Greene & P. G. M. Wuts, *Protective Groups in Organic Synthesis*, $3^{rd}$ Edition, John Wiley & Sons, 1999. The protecting groups may be removed at a convenient subsequent stage using methods known in the art.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (stereoisomers).

The term "stereoisomer" means isomers of identical constitution that differ in the spatial arrangement of their atoms. Enantiomers and diastereomers are stereoisomers wherein an asymmetrically substituted carbon atom acts as a chiral center. The term "chiral" means a molecule that is not superimposable on its mirror image, implying the absence of an axis and a plane or center of symmetry. The term "enantiomer" means one of a pair of molecular species that are mirror images of each other and are not superimposable. The term "diastereomer" means stereoisomers that are not related as mirror images.

The term "racemate" or "racemic mixture" means a compound of equimolar quantities of two enantiomeric species, wherein the compound is devoid of optical activity. The term "optical activity" means the degree to which a chiral molecule or non-racemic mixture of chiral molecules rotates the plane of polarized light.

"Geometric isomer" means isomers that differ in the orientation of substituent atoms in relationship to a carbon-carbon double bond, to a cycloalkyl ring, or to a bridged bicyclic system. Substituent atoms (other than H) on each side of a carbon-carbon double bond may be in an E or Z configuration. In the "E" configuration, the substituents are on opposite sides in relationship to the carbon-carbon double bond. In the "Z" configuration, the substituents are oriented on the same side in relationship to the carbon-carbon double bond.

The compounds of the invention may be prepared as individual isomers by either isomer-specific synthesis or resolved from an isomeric mixture. Conventional resolution techniques include combining the free base (or free acid) of each isomer of an isomeric pair using an optically active acid (or base) to form an optically active salt (followed by fractional crystallization and regeneration of the free base), forming an ester or amide of each of the isomers of an isomeric pair by reaction with an appropriate chiral auxiliary (followed by fractional crystallization or chromatographic separation and removal of the chiral auxiliary), or separating an isomeric mixture of either an intermediate or a final product using various well known chromatographic methods.

Furthermore, compounds of the invention may have one or more polymorph or amorphous crystalline forms. Said forms are included in the scope of the invention. In addition, some of the compounds may form solvates with water (i.e., hydrates) or common organic solvents. Said solvates are encompassed within the scope of this invention.

"Administering," with respect to the methods of the invention, means a method for treating, ameliorating, or preventing a disorder or disease as described herein with a compound of the invention or prodrug thereof. Such methods include administering a therapeutically effective amount of a composition of the invention at different times during the course of a therapy or concurrently in a combination form. The methods of the invention are to be understood as embracing all known therapeutic treatment regimens.

"Prodrug" means a pharmaceutically acceptable form of a functional derivative of a instant compound of the invention (or a salt thereof), wherein the prodrug may be: 1) a relatively active precursor which converts in vivo to an active prodrug component; 2) a relatively inactive precursor which converts in vivo to an active prodrug component; or 3) a relatively less active component of the compound that contributes to therapeutic biological activity after becoming available in vivo (i.e., as a metabolite). Conventional procedures for the selection and preparation of suitable prodrug derivatives are described, for example, in "Design of Prodrugs", ed. H. Bundgaard, Elsevier, 1985.

"Metabolite" means a pharmaceutically acceptable form of a metabolic derivative of a compound of the invention (or a salt thereof), wherein the derivative is a relatively less active component of the compound that contributes to therapeutic biological activity after becoming available in vivo.

The term "therapeutically effective amount" means that amount of a compound of formula (I) that is effective in an animal or human to treat, ameliorate, or prevent the symptoms of the disease or disorder being treated. The therapeutically effective amount of a compound of the invention is from about 0.001 mg/kg/day to about 300 mg/kg/day.

"Pharmaceutically acceptable carrier" means molecular entities and compositions that are of sufficient purity and quality for use in the formulation of a composition of the invention and that, when appropriately administered to an animal or a human, do not produce an adverse, allergic, or other untoward reaction. Since both human and veterinary use are included within the scope of the invention, a pharmaceutically acceptable formulation includes a composition or medicament for either human or veterinary use.

The invention further comprises mixing one or more of the compounds of the invention and a pharmaceutically acceptable carrier; and, includes those compositions resulting from such a process. Contemplated processes include both traditional and modern pharmaceutical techniques.

The composition may take a wide variety of forms to effectuate mode of administration including ocular, oral, nasal, transdermal, topical with or without occlusion, intravenous (both bolus and infusion), and injection (intraperitoneally, subcutaneously, intramuscularly, intratumorally, or parenterally). The composition may be in a dosage unit such as a tablet, pill, capsule, powder, granule, liposome, ion exchange resin, sterile ocular solution, or ocular delivery device (such as a contact lens and the like facilitating immediate release, timed release, or sustained release), parenteral solution or suspension, metered aerosol or liquid spray, drop, ampoule, auto-injector device, or suppository; for administration ocularly, orally, intranasally, sublingually, parenterally, or rectally or by inhalation or insufflation.

Compositions suitable for oral administration include solid forms such as pills, tablets, caplets, capsules (each including immediate release, timed release, and sustained release formulations), granules and powders; and, liquid forms such as solutions, syrups, elixirs, emulsions, and suspensions. Forms useful for ocular administration include sterile solutions or ocular delivery devices. Forms useful for parenteral administration include sterile solutions, emulsions and suspensions.

Alternatively, the composition may be administered in a form suitable for once-weekly or once-monthly administration. For example, an insoluble salt of the active compound may be adapted to provide a depot preparation for intramuscular injection (e.g., a decanoate salt) or to provide a solution for ophthalmic administration.

The dosage form containing the composition thereof contains an effective amount of the compound of the invention necessary to provide a therapeutic effect. The composition may contain from about 0.001 mg to about 5000 mg (preferably, from about 0.001 to about 500 mg) of a compound of the invention or salt form thereof and may be constituted into any form suitable for the mode of administration selected for a subject in need. A contemplated effective amount may range from about 0.001 mg to about 300 mg/kg of body weight per day. Preferably, the range is from about 0.003 to about 100 mg/kg of body weight per day. Most preferably, the range is from about 0.005 to about 15 mg/kg of body weight per day. The composition may be administered according to a dosage regimen of from about 1 to about 5 times per day.

For oral administration, the composition is preferably in the form of a tablet or capsule containing, e.g., 0.01, 0.05, 0.1, 0.5, 1.0, 2.5, 5.0, 10.0, 15.0, 25.0, 50.0, 100, 150, 200, 250, or 500 milligrams of the compound of the invention for the symptomatic adjustment of the dosage to the patient to be treated. Optimal dosages will vary depending on factors associated with the particular patient being treated (e.g., age, weight, diet, and time of administration), the severity of the condition being treated, the compound being employed, the mode of administration, and the strength of the preparation. The use of either daily administration or post-periodic dosing may be employed.

The oral composition is preferably formulated as a homogeneous composition wherein the compound of the invention is dispersed evenly throughout the mixture, which may be readily subdivided into dosage units containing equal amounts of a compound of the invention. Preferably, the compositions are prepared by mixing a compound of the invention (or pharmaceutically acceptable salt thereof) with one or more pharmaceutical carriers.

Because of their ease of administration, tablets and capsules represent an advantageous oral dosage unit form wherein solid pharmaceutical carriers are employed. If desired, tablets may be sugarcoated or filmcoated using standard techniques. Tablets may also be coated or otherwise compounded to provide a prolonged, control-release therapeutic effect.

Compounds of the invention may also be administered via a slow release composition, wherein the composition includes a biodegradable slow release carrier (e.g., a polymeric carrier) or a pharmaceutically acceptable non-biodegradable slow release carrier (e.g., an ion exchange carrier).

Biodegradable and non-biodegradable slow release carriers are well known in the art. Biodegradable carriers are used to form particles or matrices which retain an active agent(s)

and which slowly degrade/dissolve in a suitable environment (e.g., aqueous, acidic, basic and the like) to release the agent.

The compound of formula (I) may be incorporated for administration orally or by injection in a liquid form. The compounds may alternatively be administered parenterally via injection.

Compounds of the invention may be administered intranasally using a suitable intranasal vehicle. Compounds of the invention may be administered topically using a suitable topical transdermal vehicle or a transdermal patch. Administration via a transdermal delivery system requires a continuous rather than intermittent dosage regimen.

For ocular administration, the composition is preferably in the form of an ophthalmic composition. The ophthalmic compositions are preferably formulated as eye-drop formulations and filled in appropriate containers to facilitate administration to the eye, for example a dropper fitted with a suitable pipette.

The following are compounds of the invention, which were prepared according to the examples or by processes analogous thereto using the appropriate reagents, starting materials and methods well known to those skilled in the art. The biological data are obtained by assays described herein.

| | | Name | FAK % Inhib ave: 10 uM | CAK % inhib; 20 uM | MS m/z (M + H+) |
|---|---|---|---|---|---|
| 1 | | 1-Dimethylamino-3-[4-(3-indan-5-yl-3H-[1,2,3]triazolo[4,5-d]pyrimidin-5-ylamino)-phenoxy]-propan-2-ol | 93.64 | 101.85 | 446.0 |
| 2 | | 1-Dimethylamino-3-{4-[3-(2,4,6-trimethyl-phenyl)-3H-[1,2,3]triazolo[4,5-d]pyrimidin-5-ylamino]-phenoxy)-propan-2-ol | | | 447.9 |
| 3 | | 1-{4-[3-(3,4-Dimethoxy-phenyl)-3H-[1,2,3]triazolo[4,5-d]pyrimidin-5-ylamino]-phenoxy]-3-dimethylamino-propan-2-ol | 53.19 | | 465.9 |
| 4 | | [4-(3-Dimethylamino-propoxy)-phenyl]-(3-indan-5-yl-3H-[1,2,3]triazolo[4,5-d]pyrimidin-5-yl)-amine | 94.96 | | 429.9 |

| | Name | FAK % Inhib ave: 10 uM | CAK % inhib; 20 uM | MS m/z (M + H+) |
|---|---|---|---|---|
| 5 | (3-Indan-5-yl-3H-[1,2,3]triazolo[4,5-d]pyrimidin-5-yl)-(4-pentyloxy-phenyl)-amine | 12.36 | 25.92 | 415.2 |
| 6 | 4-[(3-Indan-5-yl-3H-[1,2,3]triazolo[4,5-d]pyrimidin-5-ylamino)-methyl]-piperidine-1-carboxylic acid tert-butyl ester | 73.05 | 28.95 | 450.8 |
| 7 | {4-[2-(4-Dimethylamino-phenyl)-vinyl]-phenyl}-(3-indan-5-yl-3H-[1,2,3]triazolo[4,5-d]pyrimidin-5-yl)-amine | −5 | 38.7 | 474.8 |
| 8 | 1-Dimethylamino-3-[4-(3-phenyl-3H-[1,2,3]triazolo[4,5-d]pyrimidin-5-ylamino)-phenoxy]-propan-2-ol | 77.40 | 92.15 | 405.9 |
| 9 | 1-[4-(3-Cyclohexyl-3H-[1,2,3]triazolo[4,5-d]pyrimidin-5-ylamino)-phenoxy]-3-dimethylamino-propan-2-ol | 23 | 85.9 | 411.9 |

| | Name | FAK % Inhib ave: 10 uM | CAK % inhib; 20 uM | MS m/z (M + H+) |
|---|---|---|---|---|
| 10 | 3-{5-[4-(3-Dimethylamino-2-hydroxy-propoxy)-phenylamino]-[1,2,3]triazolo[4,5-d]pyrimidin-3-yl]-benzonitrile | 64.74 | 11.52 | 431.0 |
| 11 | 1-{4-[3-(3,4-Difluoro-phenyl)-3H-[1,2,3]triazolo[4,5-d]pyrimidin-5-ylamino]-phenoxy}-3-dimethylamino-propan-2-ol | 65.29 | 56.04 | 441.9 |
| 12 | 1-Dimethylamino-3-[4-(3-naphthalen-2-yl-3H-[1,2,3]triazolo[4,5-d]pyrimidin-5-ylamino)-phenoxy]-propan-2-ol | 82.91 | 92.39 | 455.9 |
| 13 | 1-Dimethylamino-3-[4-(3-quinolin-6-yl-3H-[1,2,3]triazolo[4,5-d]pyrimidin-5-ylamino)-phenoxy]-propan-2-ol | 24.37 | 72.56 | 456.9 |
| 14 | 1-[4-(3-Benzothiazol-6-yl-3H-[1,2,3]triazolo[4,5-d]pyrimidin-5-ylamino)-phenoxy]-3-dimethylamino-propan-2-ol | 76.76 | 42.24 | 462.9 |

-continued

| | Name | FAK % Inhib ave: 10 uM | CAK % inhib; 20 uM | MS m/z (M + H+) |
|---|---|---|---|---|
| 15 | 1-{4-[3-(4-Cyclohexyl-phenyl)-3H-[1,2,3]triazolo[4,5-d]pyrimidin-5-ylamino]-phenoxy}-3-dimethylamino-propan-2-ol | 80.46 | 76.04 | 488.0 |
| 16 | 1-Dimethylamino-3-{4-[3-(4-morpholin-4-yl-phenyl)-3H-[1,2,3]triazolo[4,5-d]pyrimidin-5-ylamino]-phenoxy}-propan-2-ol | 50.47 | 83.09 | 491.0 |
| 17 | 1-Dimethylamino-3-{4-[3-(9H-fluoren-2-yl)-3H-[1,2,3]triazolo[4,5-d]pyrimidin-5-ylamino]-phenoxy}-propan-2-ol | 86.84 | 53.81 | 494.0 |
| 18 | {2-[(Cyclohexyl-methyl-amino)-methyl]-phenyl}-(3-indan-5-yl-3H-[1,2,3]triazolo[4,5-d]pyrimidin-5-yl)-amine | 12.19 | 20.66 | 454.5 |

-continued

| | Name | FAK % Inhib ave: 10 uM | CAK % inhib; 20 uM | MS m/z (M + H+) |
|---|---|---|---|---|
| 19 | N-(2-Diethylamino-ethyl)-4-[5-(indan-5-ylamino)-[1,2,3]triazolo[4,5-d]pyrimidin-3-yl]-benzamide | 68.76 | −63.66 | 471.5 |
| 20 | (3-{2-[(Cyclohexyl-methyl-amino)-methyl]-phenyl}-3H-[1,2,3]triazolo[4,5-d]pyrimidin-5-yl)-indan-5-yl-amine | 13 | 12.5 | 454.5 |
| 21 | {2-[(Cyclohexyl-methyl-amino)-methyl]-phenyl}-(3-{2-[(cyclohexyl-methyl-amino)-methyl]-phenyl}-3H-[1,2,3]triazolo[4,5-d]pyrimidin-5-yl)-amine | 19 | 23.3 | 539.5 |
| 22 | N-(2-Diethylamino-ethyl)-4-(3-indan-5-yl-3H-[1,2,3]triazolo[4,5-d]pyrimidin-5-ylamino)-benzamide | 98.90 | 96.88 | 471.2 |

-continued

| | Name | FAK % Inhib ave: 10 uM | CAK % inhib; 20 uM | MS m/z (M + H+) |
|---|---|---|---|---|
| 23 | Biphenyl-3-yl-(3-indan-5-yl-3H-[1,2,3]triazolo[4,5-d]pyrimidin-5-yl)-amine | 13 | 43.5 | 405.6 |
| 24 | [4-(3-Indan-5-yl-3H-[1,2,3]triazolo[4,5-d]pyrimidin-5-ylamino)-benzyl]-phosphonic acid diethyl ester | 34.04 | 24.74 | 479.2 |
| 25 | [4-(3-Indan-5-yl-3H-[1,2,3]triazolo[4,5-d]pyrimidin-5-ylamino)-phenyl]-acetic acid ethyl ester | 30 | 21.0 | 415.6 |
| 26 | 3-(3-Indan-5-yl-3H-[1,2,3]triazolo[4,5-d]pyrimidin-5-ylamino)-benzoic acid ethyl ester | 13 | 25.9 | 401.7 |
| 27 | 3-(3-Indan-5-yl-3H-[1,2,3]triazolo[4,5-d]pyrimidin-5-ylamino)-N-methyl-benzamide | 74.41 | 21.43 | 386.3 |

-continued

| | Name | FAK % Inhib ave: 10 uM | CAK % inhib; 20 uM | MS m/z (M + H+) |
|---|---|---|---|---|
| 28 | 3-[4-(3-Indan-5-yl-3H-[1,2,3]triazolo[4,5-d]pyrimidin-5-ylamino)-phenyl]-acrylic acid ethyl ester | 16 | 54.7 | 427.7 |
| 29 | (3-Indan-5-yl-3H-[1,2,3]triazolo[4,5-d]pyrimidin-5-yl)-(4-[1,2,3]thiadiazol-4-yl-phenyl)-amine | 11 | 16.3 | 413.5 |
| 30 | 4-{5-[4-(3-Dimethylamino-2-hydroxy-propoxy)-phenylamino]-[1,2,3]triazolo[4,5-d]pyrimidin-3-yl}-cyclohexane-carboxylic acid | 30 | 38.6 | 456.0 |
| 31 | 3-{5-[4-(3-Dimethylamino-2-hydroxy-propoxy)-phenylamino]-[1,2,3]triazolo[4,5-d]pyrimidin-3-yl}-cyclohexanecarboxylic acid | 21.44 | 32.93 | 456.0 |

-continued

| | | Name | FAK % Inhib ave: 10 uM | CAK % inhib; 20 uM | MS m/z (M + H+) |
|---|---|---|---|---|---|
| 32 | 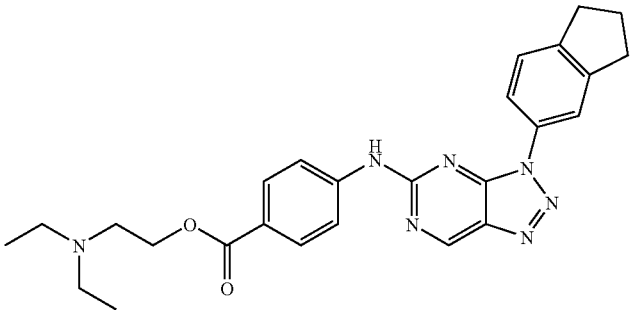 | 4-(3-Indan-5-yl-3H-[1,2,3]triazolo[4,5-d]pyrimidin-5-ylamino)-benzoic acid 2-diethylamino-ethyl ester | 30.23 | 42.00 | 471.9 |
| 33 | 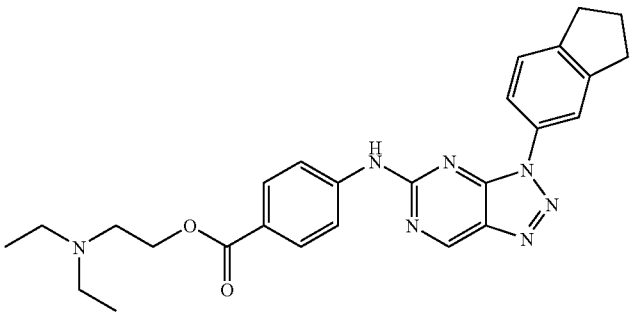 | 4-(3-Indan-5-yl-3H-[1,2,3]triazolo[4,5-d]pyrimidin-5-ylamino)-benzoic acid 2-diethylamino-ethyl ester | 28.57 | 42.00 | 471.9 |
| 34 | 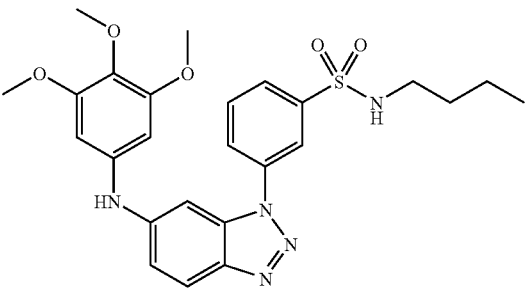 | N-Butyl-3-[5-(3,4,5-trimethoxy-phenylamino)-[1,2,3]triazolo[4,5-d]pyrimidin-3-yl]-benzene-sulfonamide | 25 | 19.0 | 513.8 |
| 35 | 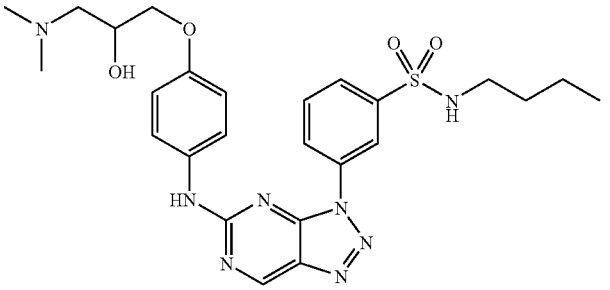 | N-Butyl-3-{5-[4-(3-dimethylamino-2-hydroxy-propoxy)-phenylamino]-[1,2,3]triazolo[4,5-d]pyrimidin-3-yl}-benzene-sulfonamide | 91.62 | | 540.9 |

-continued
| | | Name | FAK % Inhib ave: 10 uM | CAK % inhib; 20 uM | MS m/z (M + H+) |
|---|---|---|---|---|---|
| 36 | 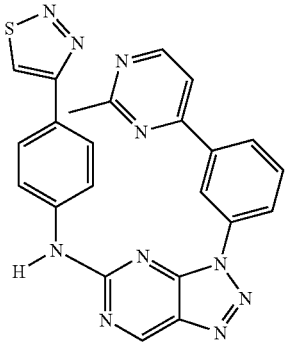 | {3-[3-(2-Methyl-pyrimidin-4-yl)-phenyl]-3H-[1,2,3]triazolo[4,5-d]pyrimidin-5-yl}-(4-[1,2,3]thiadiazol-4-yl-phenyl)-amine | −1.2 | 2.3 | 465.1 |
| 37 | 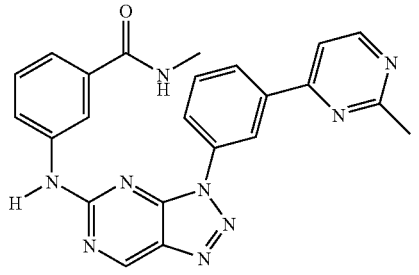 | N-Methyl-3-{3-[3-(2-methyl-pyrimidin-4-yl)-phenyl]-3H-[1,2,3]triazolo[4,5-d]pyrimidin-5-ylamino}-benzamide | −7.0 | −1.1 | 438.0 |
| 38 | 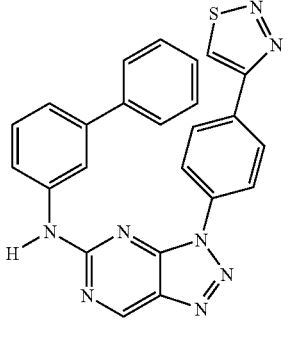 | Biphenyl-3-yl-[3-(4-[1,2,3]thiadiazol-4-yl-phenyl)-3H-[1,2,3]triazolo[4,5-d]pyrimidin-5-yl]-amine | 3.4 | 27.2 | 449.0 |
| 39 | 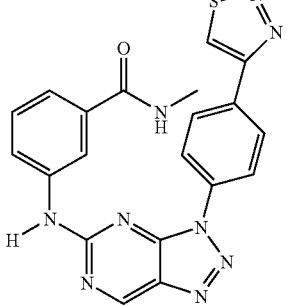 | N-Methyl-3-[3-(4-[1,2,3]thiadiazol-4-yl-phenyl)-3H-[1,2,3]triazolo[4,5-d]pyrimidin-5-ylamino]-benzamide | 3.2 | −1.5 | 430.0 |

-continued

| | Name | FAK % Inhib ave: 10 uM | CAK % inhib; 20 uM | MS m/z (M + H+) |
|---|---|---|---|---|
| 40 | N-Methyl-3-{5-[3-(2-methyl-pyrimidin-4-yl)-phenylamino]-[1,2,3]triazolo[4,5-d]pyrimidin-3-yl}-benzamide | 6.99 | −2.21 | 438.0 |
| 41 | 3-[5-(Biphenyl-3-ylamino)-[1,2,3]triazolo[4,5-d]pyrimidin-3-yl]-N-methyl-benzamide | −3.2 | 5.6 | 422.0 |
| 42 | (3,4,5-Trimethoxy-phenyl)-[3-(3,4,5-trimethoxy-phenyl)-3H-[1,2,3]triazolo[4,5-d]pyrimidin-5-yl]-amine | 35.59 | 3.40 | 469.0 |
| 43 | (1H-Indazol-5-yl)-[3-(3,4,5-trimethoxy-phenyl)-3H-[1,2,3]triazolo[4,5-d]pyrimidin-5-yl]-amine | 33.27 | 11.84 | 419.0 |

-continued

| | Name | FAK % Inhib ave: 10 uM | CAK % inhib; 20 uM | MS m/z (M + H+) |
|---|---|---|---|---|
| 44 | 3-[3-(3,4,5-Trimethoxy-phenyl)-3H-[1,2,3]triazolo[4,5-d]pyrimidin-5-ylamino]-benzene-sulfonamide | 24.7 | 10.2 | 458.0 |
| 45 | 2-[5-(1H-Indazol-5-ylamino)-[1,2,3]triazolo[4,5-d]pyrimidin-3-yl]-benzene-sulfonamide | 21.79 | 16.22 | 408.0 |
| 46 | | 29.2 | 44.9 | 447.0 |
| 47 | | 63.61 | 51.27 | 447.0 |
| 48 | | 7.44 | −37.42 | 559.0 |

|   | Name | FAK % Inhib ave: 10 uM | CAK % inhib; 20 uM | MS m/z (M + H+) |
|---|---|---|---|---|
| 49 |  | 99.50 | 44.61 | 566.2 |
| 50 | 3-{5-[4-(4-Benzyl-piperazin-1-yl)-phenylamino]-[1,2,3]triazolo[4,5-d]pyrimidin-3-yl}-N-butyl-benzene-sulfonamide | 48.40 | 31.66 | 598.3 |
| 51 | 4-[5-(3-Butylsulfonyl-phenylamino)-[1,2,3]triazolo[4,5-d]pyrimidin-3-yl]-N-(2-diethylamino-ethyl)-benzamide | 43.61 | 35.35 | 566.2 |

-continued

| Name | FAK % Inhib ave: 10 uM | CAK % inhib; 20 uM | MS m/z (M + H+) |
|---|---|---|---|
| 52 | | 47.93 | −19.14 | 573.1 |
| 53 4-{5-[4-(4-Benzyl-piperazin-1-yl)-phenylamino]-[1,2,3]triazolo[4,5-d]pyrimidin-3-yl}-N-(2-diethylamino-ethyl)-benzamide | 60.48 | 43.66 | 605.3 |

-continued
| | | Name | FAK % Inhib ave: 10 uM | CAK % inhib; 20 uM | MS m/z (M + H+) |
|---|---|---|---|---|---|
| 54 | 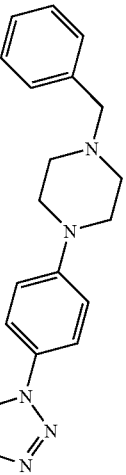 | 3-{3-[4-(4-Benzyl-piperazin-1-yl)-phenyl]-3H-[1,2,3]triazolo[4,5-d]pyrimidin-5-ylamino}-N-butyl-benzene-sulfonamide | 15.2 | 20.5 | 598.2 |
| 55 | 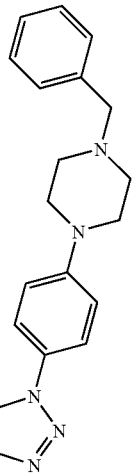 | 2-{3-[4-(4-Benzyl-piperazin-1-yl)-phenyl]-3H-[1,2,3]triazolo[4,5-d]pyrimidin-5-ylamino}-N-cyclohexyl-N-methyl-benzene-sulfonamide | 10.8 | −6.2 | 638.3 |
| 56 | 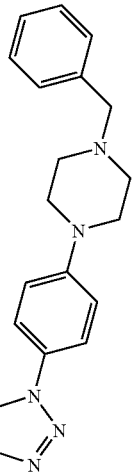 | 4-{3-[4-(4-Benzyl-piperazin-1-yl)-phenyl]-3H-[1,2,3]triazolo[4,5-d]pyrimidin-5-ylamino}-N-(2-diethylamino-ethyl)-benzamide | 75.45 | 87.27 | 605.3 |

-continued

| | Name | FAK % Inhib ave: 10 uM | CAK % inhib; 20 uM | MS m/z (M + H+) |
|---|---|---|---|---|
| 57 | | 22.0 | 34.1 | 438.0 |
| 58 | 4-(3-Benzyl-3H-[1,2,3]triazolo[4,5-d]pyrimidin-5-ylamino)-N-(2-diethylamino-ethyl)-benzamide | 58.98 | 58.00 | 445.2 |
| 59 | [4-(4-Benzyl-piperazin-1-yl)-phenyl]-(3-benzyl-3H-[1,2,3]triazolo[4,5-d]pyrimidin-5-yl)-amine | 25.0 | 47.0 | 477.2 |
| 60 | (3-Indan-1-yl-3H-[1,2,3]triazolo[4,5-d]pyrimidin-5-yl)-[3-(1H-tetrazol-5-yl)-phenyl]-amine | 26.77 | −0.99 | 397.0 |

-continued

| | Name | FAK % Inhib ave: 10 uM | CAK % inhib; 20 uM | MS m/z (M + H+) |
|---|---|---|---|---|
| 61 | N-(2-Diethylamino-ethyl)-4-(3-indan-1-yl-3H-[1,2,3]triazolo[4,5-d]pyrimidin-5-ylamino)-benzamide | 85.45 | 79.39 | 471.0 |
| 62 | N-(2-Diethylamino-ethyl)-4-{3-[3-(1H-tetrazol-5-yl)-phenyl]-3H-[1,2,3]triazolo[4,5-d]pyrimidin-5-ylamino}-benzamide | 66.72 | 45.28 | 499.0 |
| 63 | 4-{5-[3-(1H-Tetrazol-5-yl)-phenylamino]-[1,2,3]triazolo[4,5-d]pyrimidin-3-yl}-piperidine-1-carboxylic acid ethyl ester | 59.83 | 39.28 | 436.0 |
| 64 | 4-{5-[4-(2-Diethylamino-ethylcarbamoyl)-phenylamino]-[1,2,3]triazolo[4,5-d]pyrimidin-3-yl}-piperidine-1-carboxylic acid ethyl ester | 29.10 | 33.93 | 510.0 |

| | Name | FAK % Inhib ave: 10 uM | CAK % inhib; 20 uM | MS m/z (M + H+) |
|---|---|---|---|---|
| 65 | N-(2-Diethylamino-ethyl)-4-{5-[3-(1H-tetrazol-5-yl)-phenylamino]-[1,2,3]triazolo[4,5-d]pyrimidin-3-yl}-benzamide | 54.73 | 42.71 | 499.1 |
| 66 | | 87.23 | 68.08 | 421.0 |
| 67 | (3-Cyclopentyl-3H-[1,2,3]triazolo[4,5-d]pyrimidin-5-yl)-[3-(1H-tetrazol-5-yl)-phenyl]-amine | 15.37 | 44.25 | 349.0 |
| 68 | 4-(3-Cyclopentyl-3H-[1,2,3]triazolo[4,5-d]pyrimidin-5-ylamino)-N-(2-diethylamino-ethyl)-benzamide | 56.52 | 63.81 | 423.0 |

| | Name | FAK % Inhib ave: 10 uM | CAK % inhib; 20 uM | MS m/z (M + H+) |
|---|---|---|---|---|
| 69 | N-(2-Diethylamino-ethyl)-4-[3-(4-dimethylamino-benzyl)-3H-[1,2,3]triazolo[4,5-d]pyrimidin-5-ylamino]-benzamide | 27 | −11.4 | 488.1 |
| 70 | N-(2-Diethylamino-ethyl)-4-[3-(2-hydroxy-1-hydroxymethyl-2-phenyl-ethyl)-3H-[1,2,3]triazolo[4,5-d]pyrimidin-5-ylamino]-benzamide | 15 | 21.0 | 505.2 |
| 71 | 4-[3-(1H-Benzoimidazol-2-ylmethyl)-3H-[1,2,3]triazolo[4,5-d]pyrimidin-5-ylamino]-N-(2-diethylamino-ethyl)-benzamide | 27.54 | 52.77 | 485.1 |
| 72 | 3-(3-Indan-5-yl-3H-[1,2,3]triazolo[4,5-d]pyrimidin-5-ylamino)-N-(3-pyrrolidin-1-yl-propyl)-benzamide | 81.50 | 98.39 | 483.0 |
| 73 | 3-(3-Indan-5-yl-3H-[1,2,3]triazolo[4,5-d]pyrimidin-5-ylamino)-N-(2-morpholin-4-yl-ethyl)-benzamide | 31.22 | 47.55 | 485.0 |

-continued

| | | Name | FAK % Inhib ave: 10 uM | CAK % inhib; 20 uM | MS m/z (M + H+) |
|---|---|---|---|---|---|
| 74 | | N-(3-Imidazol-1-yl-propyl)-4-(3-indan-5-yl-3H-[1,2,3]triazolo[4,5-d]pyrimidin-5-ylamino)-benzamide | 72.77 | 42.66 | 479.9 |
| 75 | | 4-(3-Indan-5-yl-3H-[1,2,3]triazolo[4,5-d]pyrimidin-5-ylamino)-N-(3-pyrrolidin-1-yl-propyl)-benzamide | 77.89 | 83.98 | 482.9 |
| 76 | | 4-(3-Indan-5-yl-3H-[1,2,3]triazolo[4,5-d]pyrimidin-5-ylamino)-N-(2-morpholin-4-yl-ethyl)-benzamide | 34.70 | 10.24 | 485.0 |
| 77 | | 4-(3-Indan-5-yl-3H-[1,2,3]triazolo[4,5-d]pyrimidin-5-ylamino)-N-[3-(2-oxo-pyrrolidin-1-yl)-propyl]-benzamide | 54.18 | 72.09 | 497.0 |

-continued

| | Name | FAK % Inhib ave: 10 uM | CAK % inhib; 20 uM | MS m/z (M + H+) |
|---|---|---|---|---|
| 78 | 4-(3-Indan-5-yl-3H-[1,2,3]triazolo[4,5-d]pyrimidin-5-ylamino)-N-[3-(4-methyl-piperazin-1-yl)-propyl]-benzamide | 72.01 | 89.00 | 512.0 |
| 79 | N-(3-Imidazol-1-yl-propyl)-3-(3-indan-5-yl-3H-[1,2,3]triazolo[4,5-d]pyrimidin-5-ylamino)-benzamide | 79.99 | 86.59 | 479.9 |
| 80 | 3-(3-Indan-5-yl-3H-[1,2,3]triazolo[4,5-d]pyrimidin-5-ylamino)-N-[3-(2-oxo-pyrrolidin-1-yl)-propyl]-benzamide | 33.94 | 17.85 | 497.0 |
| 81 | 3-(3-Indan-5-yl-3H-[1,2,3]triazolo[4,5-d]pyrimidin-5-ylamino)-N-[3-(4-methyl-piperazin-1-yl)-propyl]-benzamide | 58.12 | 99.72 | 512.0 |
| 82 | 3-[4-(3-Indan-5-yl-3H-[1,2,3]triazolo[4,5-d]pyrimidin-5-ylamino)-phenoxy]-propan-1-ol | 13.51 | 5.06 | 402.9 |

-continued

| | Name | FAK % Inhib ave: 10 uM | CAK % inhib; 20 uM | MS m/z (M + H+) |
|---|---|---|---|---|
| 83 | 4-[3-(4-Cyclohexyl-phenyl)-3H-[1,2,3]triazolo[4,5-d]pyrimidin-5-ylamino]-N-(2-diethylamino-ethyl)-benzamide | 28.71 | 5.45 | 513.3 |
| 84 | N-(2-Diethylamino-ethyl)-4-[3-(3-oxazol-5-yl-phenyl)-3H-[1,2,3]triazolo[4,5-d]pyrimidin-5-ylamino]-benzamide | 46.57 | −58.92 | 498.2 |
| 85 | (3-Oxazol-5-yl-phenyl)-[3-(3-oxazol-5-yl-phenyl)-3H-[1,2,3]triazolo[4,5-d]pyrimidin-5-yl]-amine | 47.80 | 9.49 | 423.1 |

-continued

| | Name | FAK % Inhib ave: 10 uM | CAK % inhib; 20 uM | MS m/z (M + H+) |
|---|---|---|---|---|
| 86 | 4-[3-(5-Butylsulfamoyl-2-methoxy-phenyl)-3H-[1,2,3]triazolo[4,5-d]pyrimidin-5-ylamino]-N-(2-diethylamino-ethyl)-benzamide | 65.10 | 110.23 | 596.3 |
| 87 | [4-(3-Diethylamino-propoxy)-phenyl]-(3-indan-5-yl-3H-[1,2,3]triazolo[4,5-d]pyrimidin-5-yl)-amine | 81.54 | 99.54 | 458.0 |
| 88 | 2-({3-[4-(3-Indan-5-yl-3H-[1,2,3]triazolo[4,5-d]pyrimidin-5-ylamino)-phenoxy]-propyl}-methyl-amino)-ethanol | 92.29 | 103.05 | 459.9 |
| 89 | ({3-[4-(3-Indan-5-yl-3H-[1,2,3]triazolo[4,5-d]pyrimidin-5-ylamino)-phenoxy]-propyl]-methyl-amino)-acetic acid | 73.37 | 97.63 | 473.9 |

-continued

| | | Name | FAK % Inhib ave: 10 uM | CAK % inhib; 20 uM | MS m/z (M + H+) |
|---|---|---|---|---|---|
| 90 | 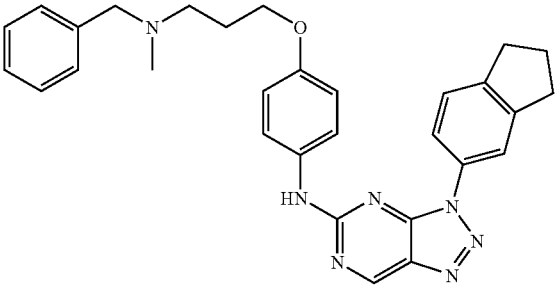 | {4-[3-(Benzyl-methyl-amino)-propoxy]-phenyl}-(3-indan-5-yl-3H-[1,2,3]triazolo[4,5-d]pyrimidin-5-yl)-amine | 31.66 | 47.54 | 506.0 |
| 91 | 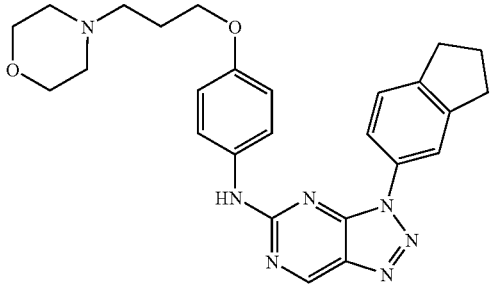 | (3-Indan-5-yl-3H-[1,2,3]triazolo[4,5-d]pyrimidin-5-yl)-[4-(3-morpholin-4-yl-propoxy)-phenyl]-amine | 10.40 | 48.73 | 471.9 |
| 92 | 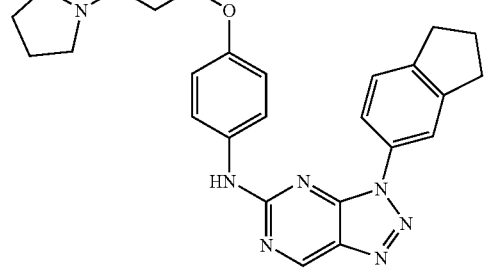 | (3-Indan-5-yl-3H-[1,2,3]triazolo[4,5-d]pyrimidin-5-yl)-[4-(3-pyrrolidin-1-yl-propoxy)-phenyl]-amine | 91.16 | 102.88 | 456.0 |
| 93 | 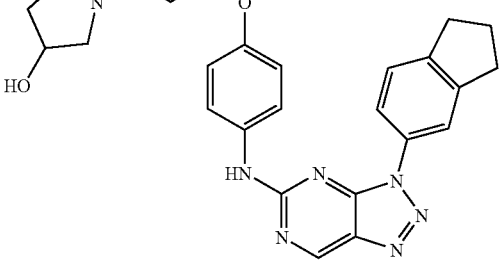 | 1-{3-[4-(3-Indan-5-yl-3H-[1,2,3]triazolo[4,5-d]pyrimidin-5-ylamino)-phenoxy]-propyl}-pyrrolidin-3-ol | 90.78 | 101.00 | 471.9 |
| 94 | 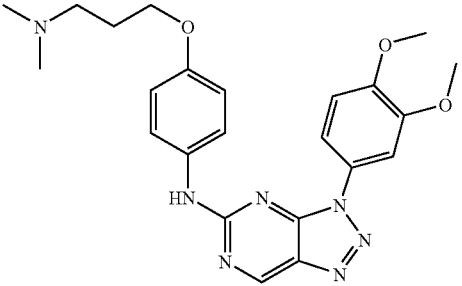 | [3-(3,4-Dimethoxy-phenyl)-3H-[1,2,3]triazolo[4,5-d]pyrimidin-5-yl]-[4-(3-dimethylamino-propoxy)-phenyl]-amine | | | |

-continued

| | Name | FAK % Inhib ave: 10 uM | CAK % inhib; 20 uM | MS m/z (M + H+) |
|---|---|---|---|---|
| 95 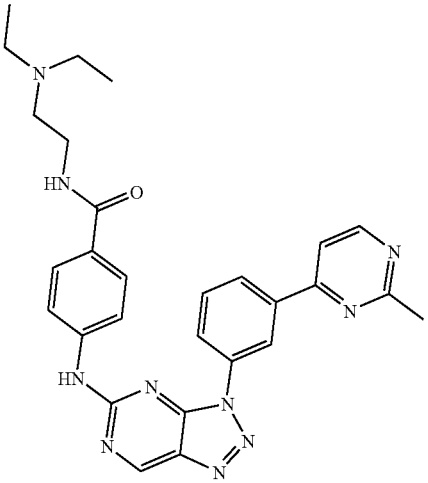 | N-(2-Diethylamino-ethyl)-4-{3-[3-(2-methyl-pyrimidin-4-yl)-phenyl]-3H-[1,2,3]triazolo[4,5-d]pyrimidin-5-ylamino}-benzamide | | | |
| 96 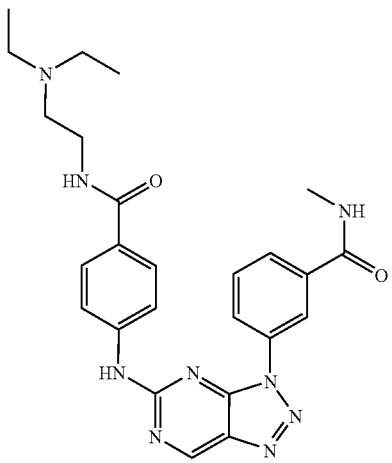 | 4-[3-(3-Methylaminocar-bonyl-phenyl)-3H-[1,2,3]triazolo[4,5-d]pyrimidin-5-ylamino]-N-(2-diethylamino-ethyl)-benzamide | | | |

The therapeutic value of the compounds of the invention may be determined by assays known in the art. For example, cdk and FAK assays are described in U.S. Pat. No. 6,716,831, which is incorporated herein in its entirety.

Abbreviations used herein are as follows:
Boc=tert-butoxycarbonyl
n-BuOH=normal-butanol
Cpd or Cmpd=compound
d=day/days
DCM=dichloromethane
DIEA=diisopropylethylamine
EDC=1-(3-dimethylaminopropyl)-3-ethylcarbodiimide hydrochloride
EtOAc=ethyl acetate
EtOH=ethanol
h/hr=hour/hours
HOBt/HOBT=hydroxybenzotriazole
M=molar
MeCN=acetonitrile
MeOH=methanol
min=minutes
NMM=N-methylmorpholine
NT=not tested
rt/RT=room temperature
THF=tetrahydrofuran
TFA=trifluoroacetic acid
TsOH=para-toluenesulfonic acid Specific compounds which are representative of this invention were prepared per the following examples and reaction sequences; the examples and the diagrams depicting the reaction sequences are offered by way of illustration, to aid in the understanding of the invention, and should not be construed to limit the invention set forth in the claims. The compounds may also be used as intermediates in subsequent examples to produce additional compounds of the invention. No attempt has been made to optimize the yields obtained in any of the reactions. One skilled in the art would know how to increase such yields through routine variations in reaction times, temperatures, solvents, and/or reagents.

Reagents were purchased from commercial sources. Nuclear magnetic resonance (NMR) spectra for hydrogen atoms were measured in the indicated solvent with (TMS) as the internal standard on a Bruker AM-360 (360 MHz) spectrometer. The values are expressed in parts per million downfield from TMS. The mass spectra (MS) were determined on a Micromass Platform LC spectrometer or an Agilent LC spectrometer using electrospray techniques. Microwave accelerated reactions were performed using either a CEM Discover or a Personal Chemistry Smith Synthesizer microwave instrument. Stereoisomeric compounds may be characterized as racemic mixtures or as separate diastereomers and enantiomers thereof using X-ray crystallography and other methods known to one skilled in the art. Unless otherwise noted, the materials used in the examples were obtained from readily available commercial suppliers or synthesized by standard methods known to one skilled in the art of chemical synthesis. The substituent groups, which vary between examples, are hydrogen unless otherwise noted.

Example 1

[4-(3-Dimethylamino-propoxy)-phenyl]-(3-indan-5-yl-3H-[1,2,3]triazolo-[4,5-d]pyrimidin-5-yl)-amine (Cpd 1)

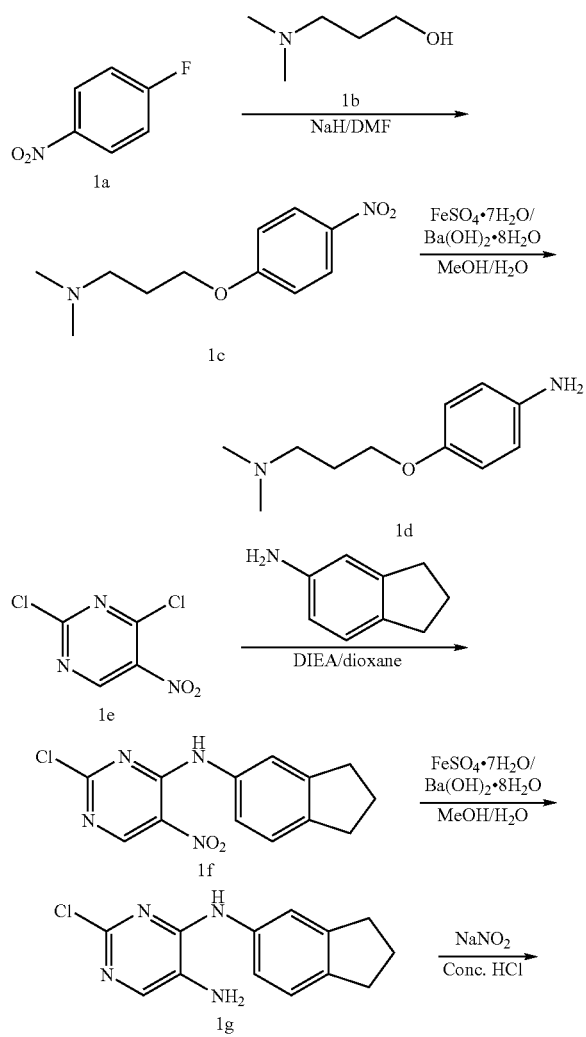

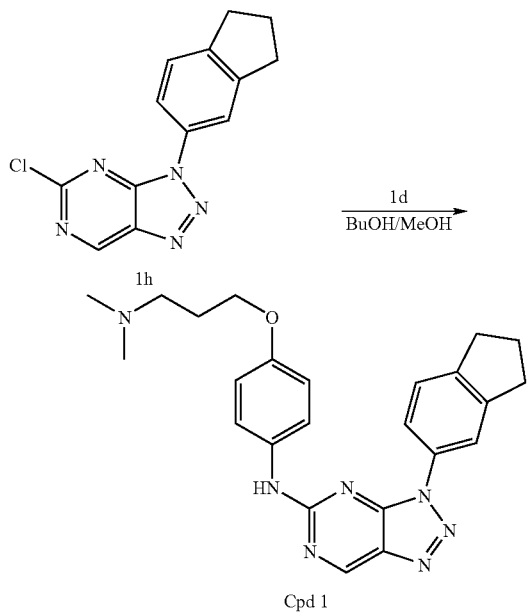

Procedure A

To a suspension of NaH (60% in oil, 3.87 g, 96.8 mmol) in DMF (80 mL) was added a solution of 3-dimethylamino-1-propanol (5 g, 48.46 mmol) in DMF (10 mL). The temperature was maintained below 35 C during the addition, and then cooled to 25 C. A solution of 1-fluoro-4-nitrobenzene (5.14 mL, 48.45 mmol) in DMF (10 mL) was added slowly to the reaction mixture. The mixture was stirred at room temperature for 4 h. The reaction mixture was carefully poured into ice-water and extracted with ether (2×300 mL). The combined organic layers were dried over $MgSO_4$ and concentrated to give desired product 1c (9.98 g, 92%). Compound 1c was used in the next reaction without further purification. MS (ES+) m/z 225.0 (M+H$^+$); $^1$H NMR (CDCl$_3$, 300 MHz): δ 2.01 (m, 2H), 2.27 (s, 6H), 2.47 (t, 2H), 4.15 (t, 2H), 6.98 (d, 2H), 8.20 (d, 2H).

Procedure B

To a suspension of iron(II) sulfate heptahydrate (18.04 g, 64.89 mmol) and barium hydroxide octahydrate (20.47 g, 64.89 mmol) in hot water (200 mL) was added a solution of Compound 1c (3 g, 13.38 mmol) in CH$_3$OH (40 mL). The reaction mixture was stirred at 80 C for about 18 h. The mixture was filtered while hot and the black residue was washed with hot CH$_3$OH. The filtrate was concentrated in vacuo to an approximate volume of 25 mL. A precipitate was collected by filtration to provide Compound 1d (1.44 g, 55%). MS (ES+) m/z 195.0 (M+H$^+$); $^1$H NMR (D$_2$O 300 MHz): δ 2.16 (m, 2H), 2.91 (s, 6H), 3.32 (t, 2H), 4.09 (t, 2H), 6.72-6.97 (m, 4H).

Procedure C

To solution of 2,4-dichloro-5-nitro-pyrimidine (1.40 g, 7.22 mmol) in dioxane (10 mL) was added a solution of 5-aminoindane (0.96 g, 7.21 mmol) in dioxane (2 mL) and DIEA (1.28 mL, 7.35 mmol). The reaction mixture was stirred at room temperature for 2 hr. The solvent was removed in vacuo and the crude product was purified by flash chromatography (silica gel, 12.5% MeOH/heptane) to give compound 1f (1.5 g, 71%). MS (ES+) m/z 290.9 (M+H$^+$); $^1$H NMR (DMSO-d$_6$, 300 MHz): δ 2.05 (m, 2H), 2.88 (m, 4H), 7.26 (m, 2H), 7.35 (s, 1H), 9.13 (s, 1H), 10.38 (s, 1H).

Compound 1g was prepared according to the method described in Procedure B and substituting 1f for 1c. MS (ES+) m/z 260.9 (M+H$^+$); $^1$H NMR (DMSO-d$_6$, 300 MHz): δ 2.05 (m, 2H), 2.88 (m, 4H), 5.25 (s, 2H), 7.25 (d, 1H), 7.31 (d, 1H), 7.50 (s, 1H), 7.65 (s, 1H), 8.55 (s, 1H).

Procedure D

To a suspension of Compound 1g (0.42 g, 1.61 mmol) in concentrated HCl (40 mL) was added NaNO$_2$ (0.111 g, 1.65 mmol). The reaction mixture was stirred at room temperature for 4 h. The mixture was cooled in an ice-bath, and KOH was added until the mixture was basic. Water (100 mL) was added to the mixture, and the mixture was then extracted with CH$_2$Cl$_2$ (2×100 mL). The organic layer was dried over MgSO$_4$, filtered, and concentrated to give Compound 1h (0.27 g, 62%). The crude product was used in the next reaction without further purification. MS (ES+) m/z 271.8 (M+H$^+$).

Procedure E

To a solution of Compound 1h (0.26 g, 0.96 mmol) in CH$_3$OH (4 mL) and n-BuOH (16 mL) was added Compound 1d (0.186 g, 0.96 mmol). The reaction mixture was stirred at 90 C for approximately 16 h, and then cooled to room temperature. The solid was collected by filtration to give Compound 1 (0.25 g, 61%). MS (ES+) m/z 429.9 (M+H$^+$); $^1$H NMR (DMSO-d$_6$, 300 MHz): δ 2.13 (m, 4H), 2.77 (s, 6H), 3.00 (m, 4H), 3.18 (t, 2H), 4.06 (t, 2H), 6.96 (d, 2H), 7.51 (d, 1H), 7.76 (d, 2H), 7.89 (d, 1H), 8.05 (s, 1H), 9.43 (s, 1H), 10.28 (s, 1H).

Example 2

1-Dimethylamino-3-[4-(3-indan-5-yl-3H-[1,2,3]triazolo[4,5-d]pyrimidin-5-ylamino)-phenoxy]-propan-2-ol (Cpd 2)

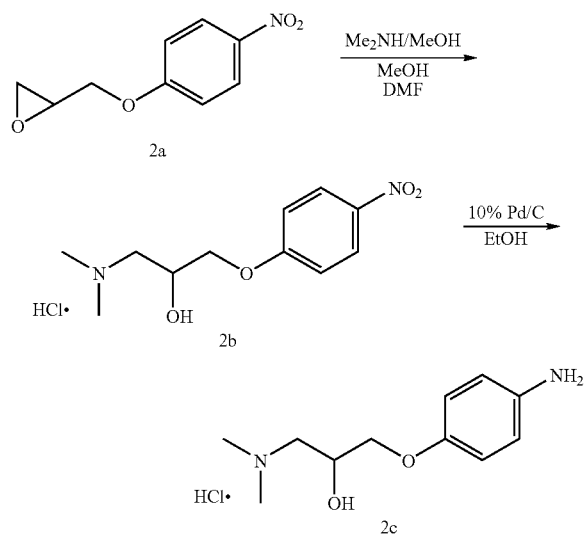

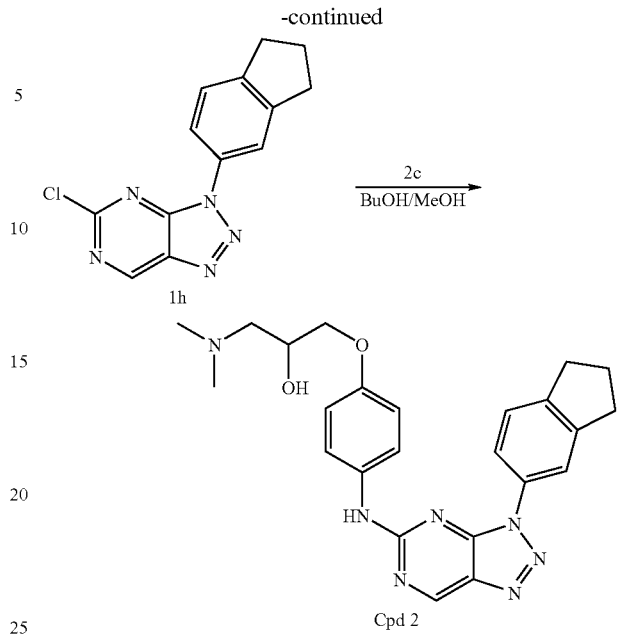

Procedure F

To a solution of 2-(4-nitrophenoxymethyl)-oxirane (0.1 mol, 19.52 g) in methanol (150 mL) and dimethyl formamide (50 mL) was added a 2 M solution of dimethylamine in methanol (0.2 mol, 100 mL), and the mixture was stirred at rt overnight. The solvent was evaporated, and the residue was dissolved in a mixture of methylene chloride (300 mL) and methanol (30 mL). A portion of 1 N HCl in diethyl ether (150 mL) was added dropwise, and an oil formed. The oil was separated (ethereal layer was decanted), and the oil was dried under vacuum, yielding 1-dimethylamino-3-(4-nitro-phenoxy)-propan-2-ol (16.6 g) as its hydrochloride salt. MS (ES+) m/z: 240.9 (M+H$^+$). The compound was used as such for the next reaction.

Procedure G

A suspension of Compound 2b (0.06 mol, 16.6 g) and palladium on carbon (10%, 1.5 g) in ethanol (200 mL) was hydrogenated in a Parr apparatus overnight at 30 psi. The catalyst was removed via filtration, and the residue was evaporated, yielding a gummy solid. The solid was recrystallized from ethanol to yield 1-(4-amino-phenoxy)-3-dimethylamino-propan-2-ol (7.52 g) as its hydrochloride salt. $^1$H NMR (DMSO-d$_6$): δ 6.70 (2H, d, J=8.7 Hz), 6.56 (2H, d, J=8.7 Hz), 5.91 (1H, s br), 4.23 (1H, s br), 3.68 (2H, m), 3.34-3.10 (3H, m), 2.81 (6H, s).

The title compound 2 was prepared using the method described in Example 1, substituting compound 2c for compound 1d in Procedure E. The crude product was purified by normal phase chromatography, using a gradient of ethyl acetate (10% to 50%) in heptane to give Compound 2. MS (ES+) m/z 446.0 (M+H$^+$); $^1$H NMR (DMSO-d$_6$, 300 MHz): δ 2.12 (m, 2H), 2.84 (s, 3H), 2.87 (s, 3H), 2.98 (m, 4H), 3.29 (m, 2H), 3.98 (m, 2H), 4.35 (m, 1H), 6.01 (broad, 1H), 6.98 (d, 2H), 7.48 (d, 1H), 7.77 (d, 2H), 7.88 (d, 1H), 8.02 (s, 1H), 9.41 (s, 1H), 10.29 (s, 1H).

Example 3

1-Dimethylamino-3-{4-[3-(2,4,6-trimethyl-phenyl)-3H-[1,2,3]triazolo[4,5-d]pyrimidin-5-ylamino]-phenoxy}-propan-2-ol (Cpd 3)

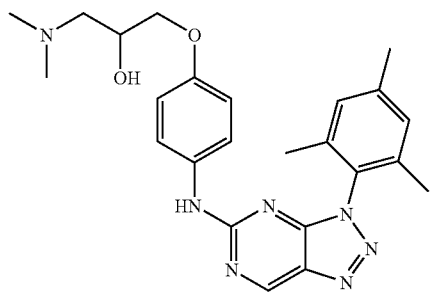

The title compound 3 was prepared using the method described in Example 1, substituting 2,4,6-trimethylaniline for 5-aminoindane in Procedure C and using an adaptation of Procedure E. The crude product was purified by reverse phase preparative HPLC using a gradient of acetonitrile (25% to 45%) in water with trifluoroacetic acid (0.1%), to give give the trifluoroacetic acid salt of compound 3. MS (ES+) m/z 447.9 (M+H$^+$); $^1$H NMR (DMSO-d$_6$, 300 MHz): δ 2.84 (s, 3H), 2.87 (s, 3H), 3.29 (m, 2H), 3.87 (s, 3H), 3.88 (s, 3H), 3.98 (m, 2H), 4.31 (m, 1H), 6.01 (d, 1H), 6.98 (d, 2H), 7.25 (d, 1H), 7.65 (dd, 1H), 7.77 (m, 3H), 9.45 (s, 1H), 10.29 (s, 1H).

Example 4

3-(3-Indan-5-yl-3H-[1,2,3]triazolo[4,5-d]pyrimidin-5-ylamino)-N-(3-pyrrolidin-1-yl-propyl)-benzamide (Cpd 4)

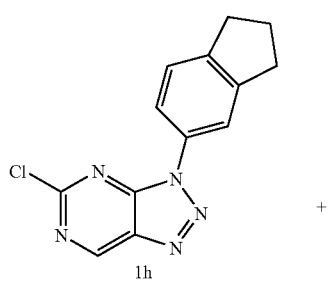

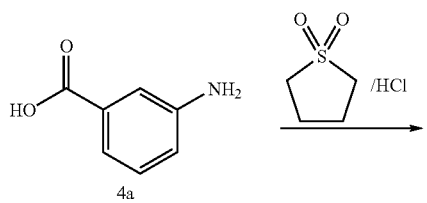

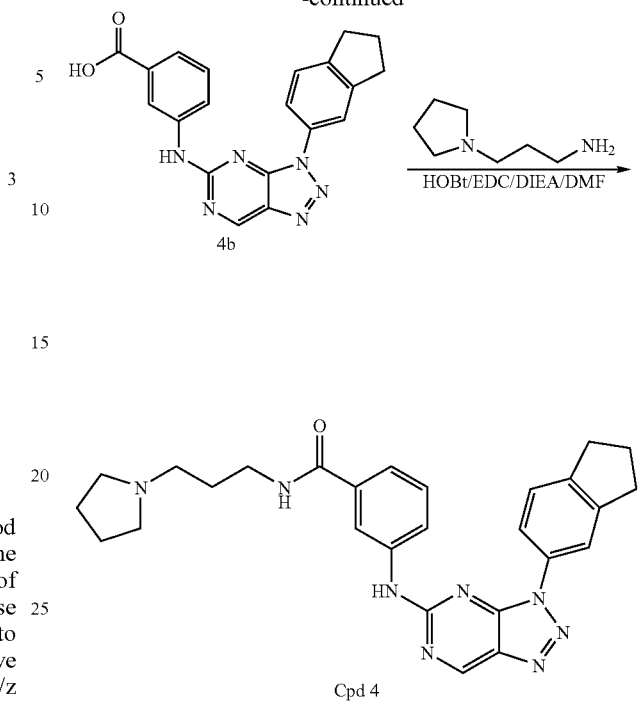

Procedure H

To a solution of Compound 1h (0.247 g, 0.91 mmol) and 3-aminobenzoic acid (0.1 g, 0.73 mmol) in sulpholane (4 mL) was added a solution of HCl (1.0 M in Et$_2$O, 0.9 mL, 0.9 mmol). The reaction mixture was stirred at 140 C for 30 hr. and then cooled to room temperature. The solid was collected by filtration, washed with acetone, and dried. The crude compound 4b was used in the next reaction without further purification. MS (ES+) m/z 372.9 (M+H$^+$).

Procedure I

To a solution of Compound 4b (0.05 g, 0.13 mmol) in DMF (3 mL) were added HOBt (0.016 g, 0.12 mmol), EDC (0.023 g, 0.12 mmol) and DIEA (0.09 mL, 0.52 mmol). The mixture was stirred at room temperature for 30 min. To the mixture was added N-(3-aminopropyl)pyrrolidine (0.017 g, 0.13 mmol). The reaction mixture was stirred at 90° C. for 5 hr and at room temperature for 7 days Water (5 mL) was added to the mixture. The aqueous layer was extracted with EtOAc (3×5 mL). The combined organic layers were washed with H$_2$O (10 mL), dried over MgSO$_4$, and concentrated. The resultant solid was washed with MeOH and dried to give compound 4. MS (ES+) m/z 483.0 (M+H$^+$); $^1$H NMR (DMSO-d$_6$, 300 MHz): δ 1.65 (m, 6H), 2.14 (m, 2H), 3.42 (m, 6H), 2.95 (m, 4H), 3.29 (m, 2H), 7.41 (m, 2H), 7.47 (m, 1H), 7.80 (d, 1H), 7.95 (d, 1H), 8.01 (s, 1H), 8.45 (s, 1H), 8.50 (t, 1H), 9.48 (s, 1H), 10.49 (s, 1H).

Example 5
3-(3-Indan-5-yl-3H-[1,2,3]triazolo[4,5-d]pyrimidin-5-ylamino)-N-(2-morpholin-4-yl-ethyl)-benzamide (Cpd 5)
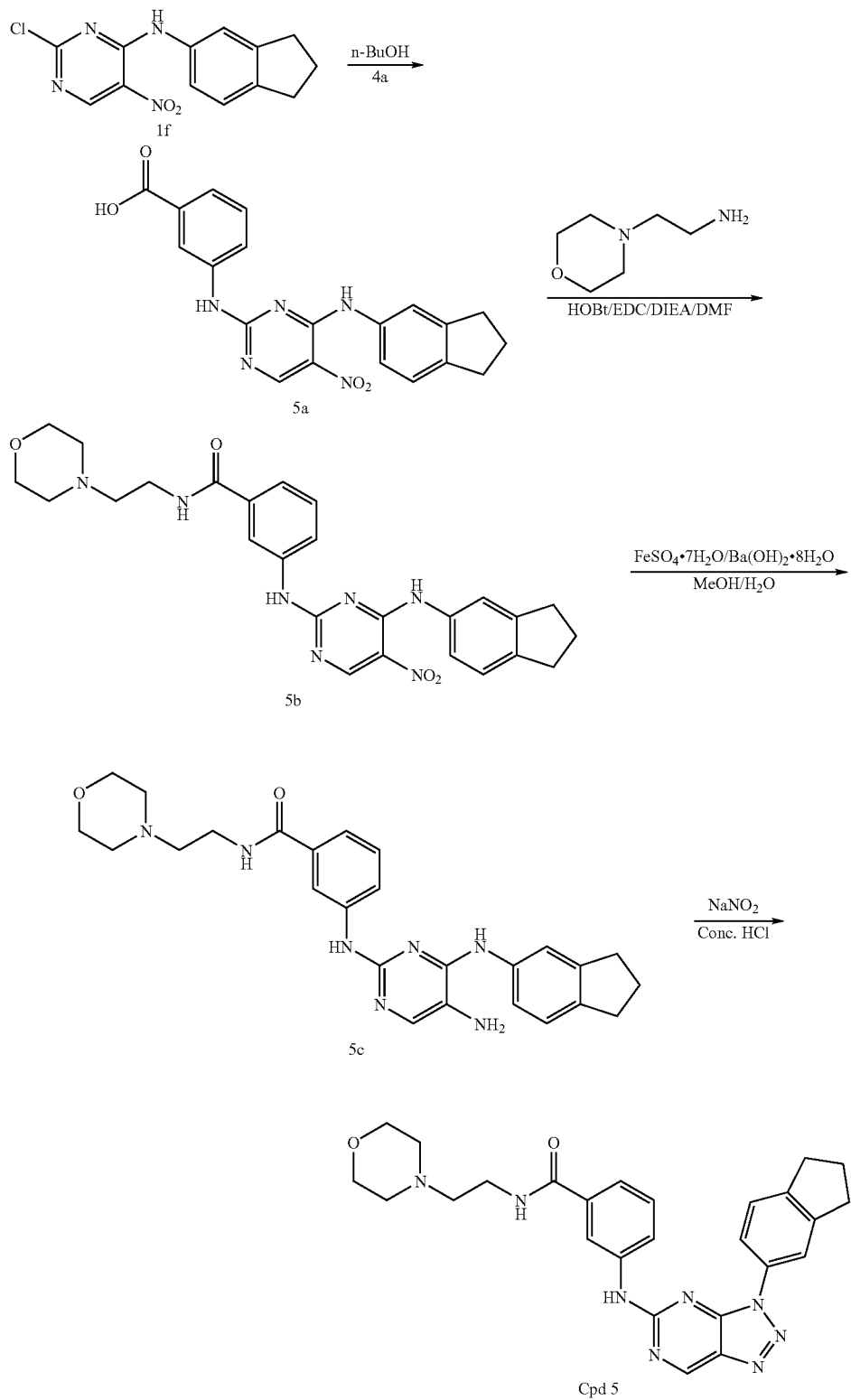

Procedure J

To a solution of 1f (0.5 g, 1.72 mmol) in n-BuOH (40 mL) was added Compound 4a (0.236 g, 1.72 mmol). The reaction mixture was stirred at 90° C. for 2 hr, and cooled to room temperature. The solid was collected by filtration to give compound 5a, which was used in the next reaction without further purification. MS (ES+) m/z 391.8 (M+H$^+$); $^1$H NMR (DMSO-d$_6$, 300 MHz): δ 2.11 (m, 2H), 2.94 (m, 4H), 7.28 (m, 3H), 7.51 (m, 1H), 7.68 (d, 1H), 8.00 (m, 2H), 9.16 (s, 1H), 10.38 (s, 1H), 12.99 (s, 1H).

Compound 5b was prepared using the method described in Example 4, substituting 4-(2-aminoethyl)morphline for N-(3-aminopropyl)pyrrolidine and substituting 5a for 4b in Procedure I. The solid was washed with EtOAc and dried to give pure compound 5b. MS (ES+) m/z 503.9 (M+H$^+$).

Compound 5c was prepared using the method described in Example 1, substituting 5b for 1c in Procedure B. The crude product was used in the next reaction without further purification. MS (ES+) m/z 473.9 (M+H$^+$).

The title Compound 5 was prepared using the method described in Example 1, substituting 5c for 1g in Procedure D. The crude product was purified by reverse phase preparative HPLC using a gradient of acetonitrile (20% to 40%) in water with trifluoroacetic acid (0.1%), to give the trifluoroacetic acid salt of Compound 5. MS (ES$^+$) m/z 485.0 (M+H$^+$); $^1$H NMR (DMSO-d$_6$, 300 MHz): δ 2.12 (m, 2H), 2.99 (m, 4H), 3.15 (m, 2H), 3.56 (m, 2H), 3.65 (m, 4H), 4.02 (m, 2H), 7.52 (m, 3H), 7.98 (d, 1H), 8.03 (s, 1H), 8.45 (s, 1H), 8.72 (s, 1H), 9.50 (s, 1H).

Example 6

3-[4-(3-indan-5-yl-3H-[1,2,3]triazolo[4,5-d]pyrimidin-5-ylamino)-phenoxy]-propan-1-ol (Cpd 6)

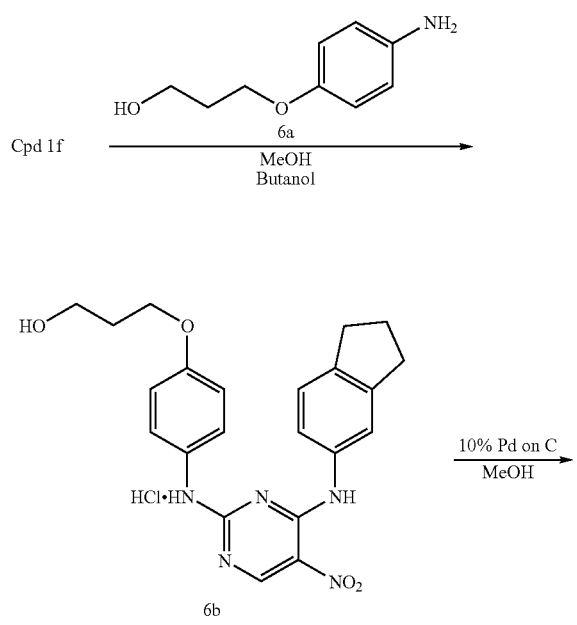

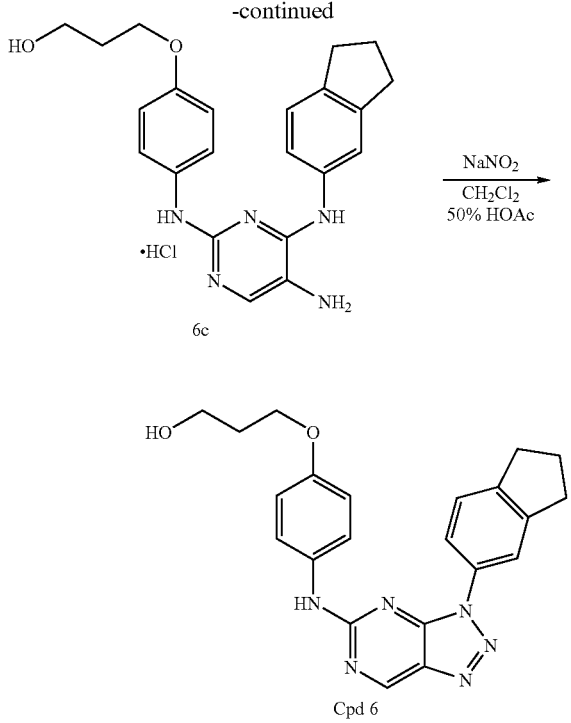

Procedure J (2-Chloro-5-nitro-pyrimidin-4-yl)-indan-5-yl-amine, Compound 1f, (15 mmol, 4.36 g), 3-(4-aminophenoxy)-propan-1-ol (16.5 mmol, 2.76 g) and methanol (10 mL) were combined in butanol (30 mL), and the mixture was stirred at 90° C. for 2.5 h. The mixture was allowed to cool to rt, filtered, and washed with Et$_2$O (2×25 mL) to yield Compound 6b (5.20 g) as its hydrochloride salt. MS (ES+) m/z 421.9 (M+H$^+$).

Procedure K

To a solution Compound 6b (10.9 mmol, 5.0 g) in methanol (125 mL), was added palladium on carbon (10%, 1.5 g), and the mixture was hydrogenated for 2.5 hr in a Parr apparatus at 40 psi. The catalyst was removed via filtration over Celite. Upon concentration of the filtrate, Compound 6c was obtained as its hydrochloride salt (4.50 g). MS (ES+) m/z 392.2 (M+H$^+$).

Procedure L

To a suspension of Compound 6c (11.5 mmol, 4.5 g) in 50% acetic acid (100 mL), sodium nitrite (12.9 mmol, 0.89 g) and methylene chloride (200 mL) were added, and the mixture was stirred for 20 min at rt. A portion of H$_2$O (200 mL) and CH$_2$Cl$_2$ (200 mL) were added, and the organic layer was separated, washed with saturated NaHCO$_3$ (2×150 mL), dried over MgSO$_4$ and treated with charcoal to remove color. The mixture was filtered and the filtrate was evaporated to yield the title compound 6 (1.35 g). MS (ES+) m/z 402.9 (M+H$^+$).

Example 7

2-({3-[4-(3-Indan-5-yl-3H-[1,2,3]triazolo[4,5-d]pyrimidin-5-ylamino)-phenoxy]-propyl}-methylamino)-ethanol (Cpd 7)

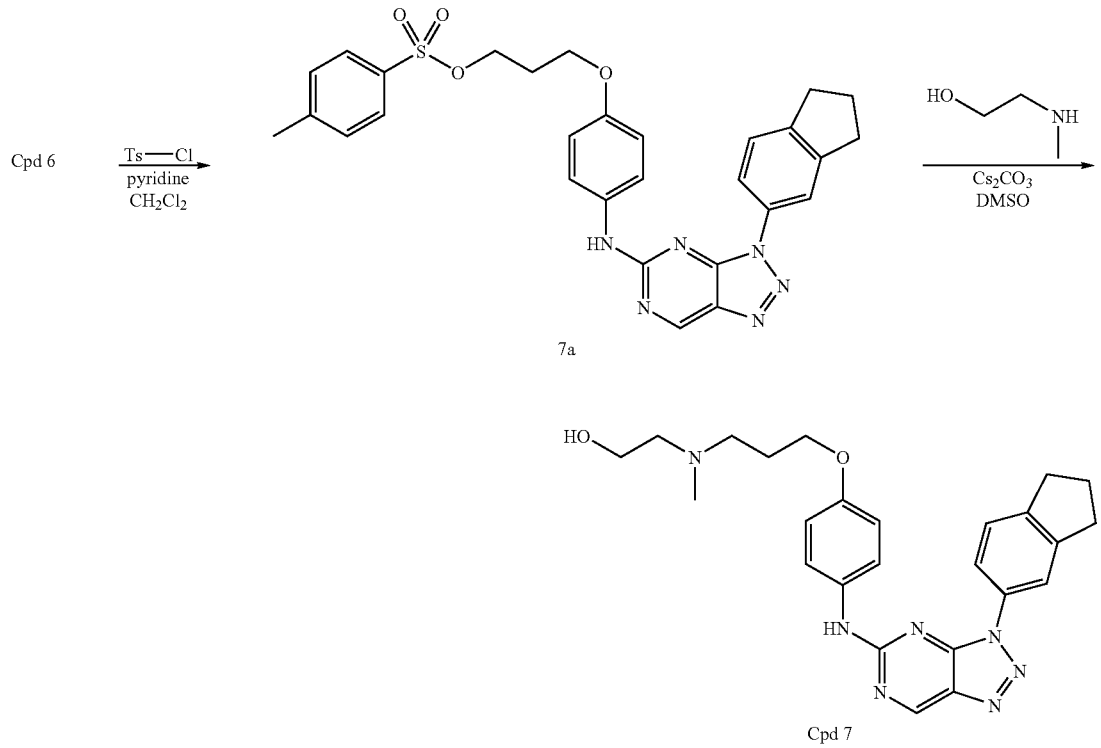

Procedure M

To a suspension of Compound 6 (3.35 mmol, 1.35 g) and pyridine (1 mL) in methylene chloride (50 mL), p-toluenesulfonyl chloride (4.19 mmol, 0.89 g) was added, and the mixture was stirred for 4 d at rt. The reaction had not gone to completion. The mixture was evaporated to dryness, and 1,4-dioxane (75 mL), pyridine (5 mL), and p-toluenesulfonyl chloride (4.19 mmol, 0.89 g) were added and the mixture was stirred for 16 hr. Methylene chloride was added, and the organic layer was washed sequentially with saturated aqueous NaHCO$_3$ and ammonium chloride. The organic layer was dried over magnesium sulfate, filtered, and concentrated to yield Compound 7a (1.30 g). MS (ES+) m/z 556.8 (M+H$^+$).

Procedure N

Compound 7a (0.1 mmol, 56 mg), 2-methylamino-ethanol (0.2 mmol), and cesium carbonate (0.4 mmol, 130 mg) were combined in dimethyl sulfoxide (2 mL), and the mixture was heated for 10 min at 120° C. in a microwave (100 Watt). The title compound 7 was isolated from the reaction mixture via reverse phase HPLC (30-90% CH$_3$CN in H$_2$O containing 0.1% TFA). MS (ES+) m/z 459.9 (M+H$^+$).

Using the procedures of Example 7 and the appropriate reagents, starting materials, and methods known to those skilled in the art, the following compounds of formula (I), wherein R$^1$ and R$^2$ are as shown, may be prepared including:

| R$^1$ | R$^2$ | Yield (mg) | m/z (M + H$^+$) (ES+) |
|---|---|---|---|
| Me | HOOC—(CH$_2$)— | 12.0 | 473.9 |
| Me | PhCH$_2$— | 13.7 | 506.0 |
| —(CH$_2$)$_2$—O—(CH$_2$)$_2$— | | 23.1 | 471.9 |
| —(CH$_2$)$_4$— | | 26.2 | 456.0 |
| —(CH$_2$)—CHOH—(CH$_2$)$_2$— | | 39.8 | 471.9 |

Example 8

4-(3-Indan-5-yl-3H-[1,2,3]triazolo[4,5-d]pyrimidin-5-ylamino)-benzoic acid 2-diethylamino-ethyl ester (4)

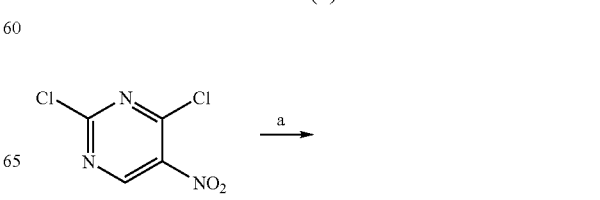

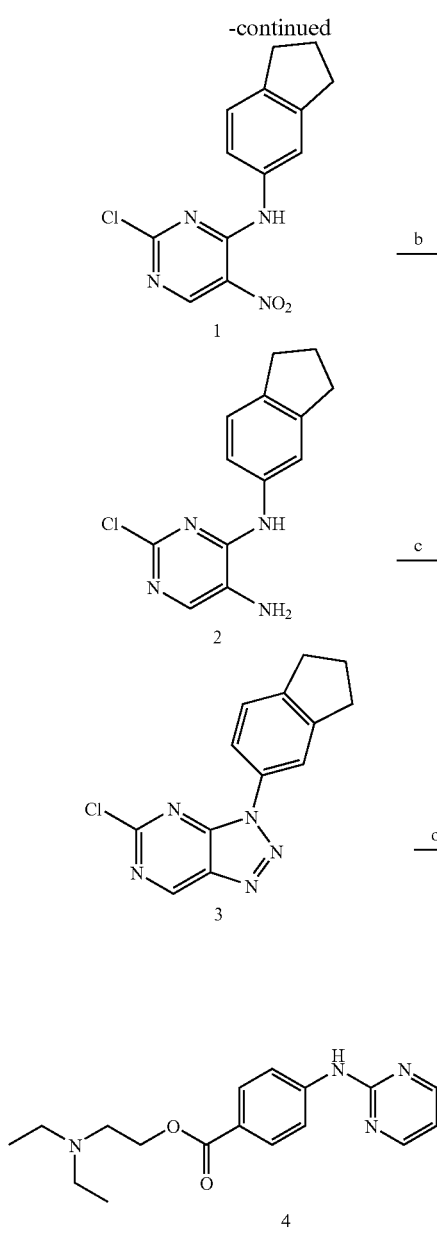

gen (3 cycles). The reaction mixture was vigorously stirred under hydrogen for 6 hr. The vessel containing the reaction mixture was evacuated and filled with nitrogen (3 cycles), filtered through celite, and the resulting filtrate was concentrated to provide crude 2-chloro-$N^4$-indan-5-yl-pyrimidine-4,5-diamine, (2).

To a solution of crude (2) in $CH_2Cl_2$ (65 mL) was added 50% aq. HOAc (65 mL) and sodium nitrite (1.96 g, 28.4 mmol). The mixture was vigorously stirred at 25° C. for 1 hr. The layers were separated and the aqueous layer was extracted with $CH_2Cl_2$ (3×). The combined organic layer was washed successively with $H_2O$ and brine, then dried ($MgSO_4$), filtered, and concentrated. The residue was purified by flash chromatography (0-5%; ethyl acetate/heptane) to furnish (3) (3.2 g, 11.8 mmol). MS m/z (M+H),+ calcd 272.1. found 272.0.

4-(3-Indan-5-yl-3H-[1,2,3]triazolo[4,5-d]pyrimidin-5-ylamino)-benzoic acid 2-diethylamino-ethyl ester (4)

To a solution of (3) (40 mg, 0.15 mmol) in DMSO (1.6 mL) was added 2-(diethylamino)ethyl-4-aminobenzoate (38 mg, 0.16 mmol). The mixture was irradiated at 140° C. for 10 min. After cooling to room temperature, the mixture was purified by reverse-phase chromatography to furnish the desired product (4) (32.2 mg, 0.046 mmol) as a trifluoroacetate salt. MS calcd. for $C_{26}H_{30}N_7O_2$ m/z calcd 472.24 (M+H),+ found 472.24.

Example 9

N-(2-Diethylamino-ethyl)-4-(3-indan-5-yl-3H-[1,2,3]triazolo[4,5-d]-pyrimidin-5-ylamino)-benzamide (7)

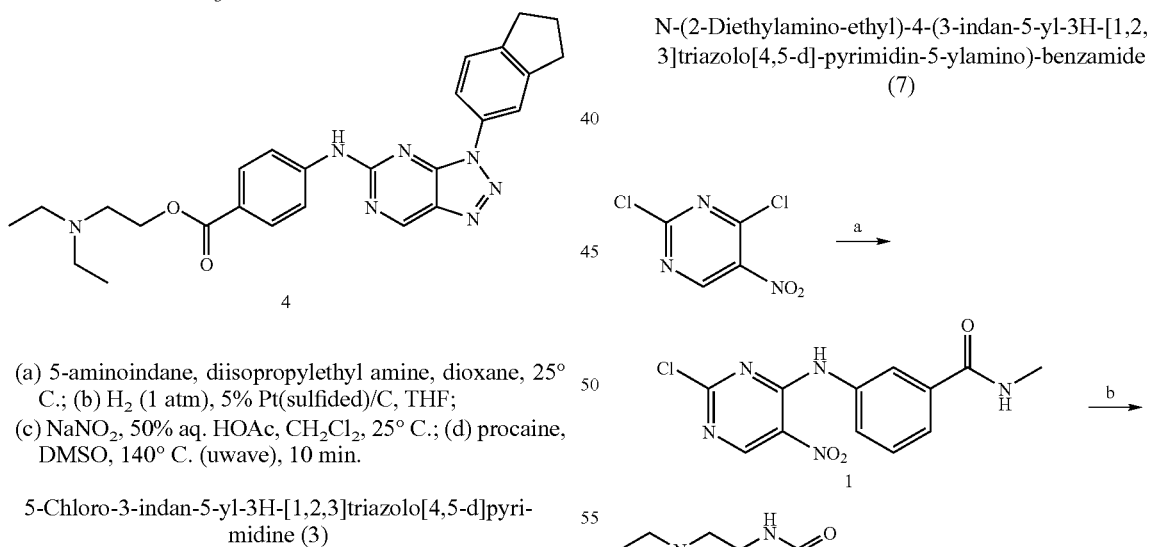

(a) 5-aminoindane, diisopropylethyl amine, dioxane, 25° C.; (b) $H_2$ (1 atm), 5% Pt(sulfided)/C, THF;
(c) $NaNO_2$, 50% aq. HOAc, $CH_2Cl_2$, 25° C.; (d) procaine, DMSO, 140° C. (uwave), 10 min.

5-Chloro-3-indan-5-yl-3H-[1,2,3]triazolo[4,5-d]pyrimidine (3)

To 2,4-dichloro-5-nitropyrimidine (5.0 g, 25.8 mmol) in dioxane (35 mL) was added a solution of 5-aminoindane (3.43 g, 25.8 mmol) in dioxane (9 mL) and diisopropylethyl amine (4.5 mL, 25.8 mmol). The mixture was stirred at 25° C. for 1 hr and then concentrated to a residue to provide crude (2-chloro-5-nitro-pyrimidin-4-yl)-indan-5-yl-amine, (1).

To a nitrogen purged reaction vessel was added 5% Pt (sulfided)/C (1.04 g), THF (15 mL), and crude (1) in THF (104 mL). The vessel was evacuated and filled with nitrogen (3 cycles) and subsequently evacuated and filled with hydro-

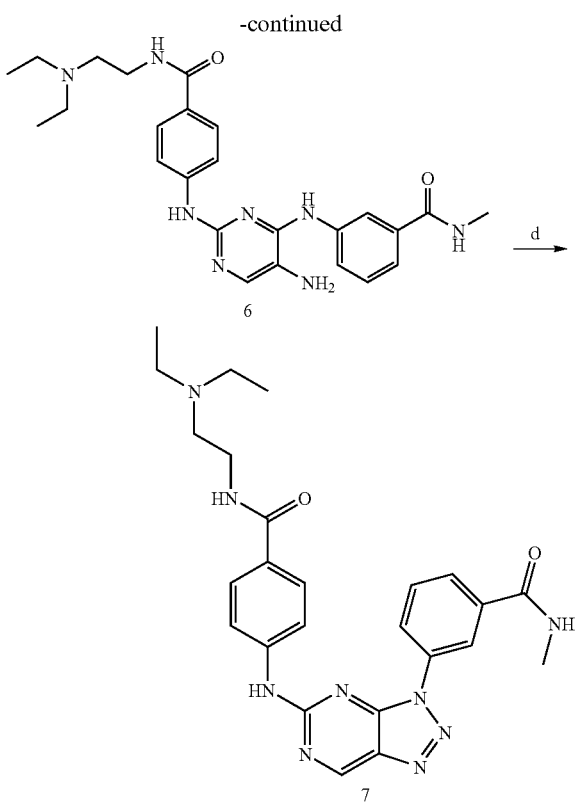

(a) 3-amino-N-methyl-benzamide, CsHCO$_3$, isopropyl alcohol/dimethylformamide/water, rt, 90 min; (b) procainamide, isopropyl alcohol/dimethylformamide, 50° C., 20 h; (c) HOAc, Zn, 15 min, rt then silica gel SPE (d) NaNO$_2$, 18 h, rt. then C-18 SPE To a solution of 2,4-dichloro-5-nitropyrimidine (25.0 mg, 0.13 mmol) in THF (0.2 mL) was added a solution of 3-amino-N-methyl-benzamide (19.5 mg, 0.13 mmol) in isopropyl alcohol (0.5 mL)/dimethylformamide (0.3 mL), and CsHCO$_3$ (25.2 mg, 0.13 mmol) in water (0.016 mL total volume). The mixture was stirred at rt for 1.5 hr at which time 4-amino-N-(2-diethylamino-ethyl)-benzamide HCl (procainamide: hydrochloride) (38.9 mg, 0.14 mmol) in isopropyl alcohol (0.5 mL)/dimethylformamide (0.3 mL) was added. The mixture was stirred at 50° C. for 20 hr. cooled to rt, and acetic acid (0.1 mL) was added. To the resulting slurry was added Zn dust (45 mg, 0.69 mmol); after stirring for 15 min at rt, the reaction solution was loaded onto a 1 g silica gel SPE cartridge and eluted with 6 mL of MeOH. The eluent was concentrated at reduced pressure, dried at approximately 1 mm Hg for 18 hr. and re-suspended in MeOH (1.0 mL). To this slurry was added HOAc (0.05 mL) and sodium nitrite (0.09 g, 1.3 mmol) in water (total volume 0.2 mL). The mixture was stirred at rt for 11 hr. loaded onto a 1 g C-18 SPE cartridge, and eluted with 6 mL of MeOH. The eluent was concentrated and the resulting residue was purified by reverse-phase liquid chromatography using a gradient of 90:10 (water:acetonitrile, with 0.1% TFA) to 10:90 (water:acetonitrile, with 0.1% TFA) to furnish (7) (0.0128 g, 0.018 mmol) as the bis TFA salt. HRMS (ES-TOF) calcd. for C$_{25}$H$_{30}$N$_9$O$_2$ m/z 488.2522 (M+H),$^+$ found: 488.2514.

BIOLOGICAL EXAMPLES

FAK Assay

Compound effects on the tyrosine kinase activity of Focal Adhesion Kinase were assessed with an in vitro FAK ELISA kinase assay. This assay measures the incorporation of phosphate from ATP into a FAK substrate protein using an antibody specific for phospho-tyrosine.

500 ng of FAK$_{substrate}$, a purified recombinant fusion protein of GST and a 73 amino acid region surrounding the Tyr$_{397}$ human FAK autophosphorylation site, was coated in a high-protein binding polystyrene 96 well plate overnight in a buffer containing 50 mM Hepes, pH 7.5, 150 mM NaCl, 0.1 mM Na-oVO$_4$, 0.1 mM NaF and 1 protease inhibitor tablet/10 mL (Complete Mini-EDTA-free, Roche). The next day this solution was removed and the wells were incubated with 0.2% BSA in 50 mM Hepes, pH 7.5, 150 mM NaCl, 0.2 mM PMSF for 1 hour at 30° C. to block unoccupied protein binding sites. The wells were then washed with 50 mM Hepes, pH 7.5, 150 mM NaCl, 0.1% Tween 20. The kinase reaction was performed with 25 ng/well of FAK enzyme (a purified recombinant full-length Flag-tagged human FAK protein made in baculovirus infected insect cells) in 0.1 mL of a buffer containing 25 mM Hepes, pH 7.5, 5 mM MgCl$_2$, 0.5 mM MnCl$_2$, 10 uM NaoVO$_4$, 0.2 mM PMSF. Compounds were added from 30% DMSO stock solutions for a screening concentration of 10 uM or IC$_{50}$ determinations from 50 uM in half-log dilutions. The reaction is initiated with addition of ATP to a final concentration of 2 uM and incubated at 30° C. for 1 hour. Following the kinase reaction step, the wells were washed and incubated with 50 ng of Horseradish Peroxidase conjugated anti-phosphotyrosine antibody (PT-66 HRP, Sigma) in 0.1 mL wash buffer for 1 hour at 30° C. Wells were then washed and 0.1 mL HRP substrate, Tetra-methyl Benzidine (Sigma) was added and the color reaction allowed to proceed for 2-3 minutes followed by the addition of 0.1 mL of 1N H$_2$SO$_4$ to stop the HRP reaction. Percent inhibition of FAK kinase activity was calculated by comparing compound containing wells to wells treated with diluent only. Background was subtracted from all wells and was defined as the activity of FAK using 500 ng/well of BSA as a substrate. IC$_{50}$ values were obtained using Prism data analysis software.

CAK Assay

Cloning and Expression of the CAK Subunits

Cyclin Dependent Kinase Activating Kinase (CAK) is a complex of proteins that phosphorylates a well-conserved threonine (Thr) residue in all mammalian cyclin dependent kinases (cdks). The CAK complex can also phosphorylate several components of the transcriptional machinery, such as the C-terminal domain (CTD) of RNA polymerase II in the TFIIH transcription complex. The CAK complex localizes to the nucleus, and is composed of three proteins: Cdk7, Cyclin H, and MAT-1. The exemplified method teaches the cloning and expression CAK subunits, particularly a human Cdk7 and a human Cyclin H. The method of the present invention exemplified herein is equally applicable to the cloning and expression of any CAK subunit, such as variants, structural or functional polymorphisms of the human Cdk7 or the human Cyclin H, or their orthologs in other animals such as rat, mouse, pig, dog and monkey.

The genes for human cdk7 and human cyclin H were obtained from Incyte as verified sequence clones no.'s 2496221 and 2452652, respectively. The Genbank accession numbers for human cdk7 and human cyclin H are X79193 and U11791, respectively.

The gene encoding residues 2 (Alanine) to 346 (Phe) of the human Cdk7 protein was amplified by PCR in order to fuse the gene, in the correct translational reading frame, downstream of a flag-epitope coding sequence on a vector pVL-1392-Flag. The PVL-1392-Flag vector is a modification of the commercially available pVL-1392 baculovirus transfer vector (Becton-Dickenson). It is designed to append a flag-epitope, for example, consisting of the amino acid sequence MDYKDDDDKAA (SEQ ID NO: 1), to the N-terminal of a protein encoded by a gene inserted at a Not 1 site on the vector. The PCR primers used for the amplification and modification of the human cdk7 gene were, SEQ ID NO: 2, 5'-TTAAGGCGGCCGCTCTGGACGTGAAGTCTCGG and SEQ ID NO: 3, 5'-TTTGAATTCTCTTTAAAAAATT-AGTTTCTTGGGC. The cdk7 PCR fragment was subcloned into pCR2.1 (Invitrogen), excised with restriction enzymes Not 1 (New England Biolabs) and Eco R1 (New England Biolabs), and inserted into the vector pVL-1392-Flag by DNA ligation. The Flag-Cdk7 coding sequence on the vector was confirmed via DNA sequencing and was presented in SEQ ID NO: 4. The deduced amino acid sequence of the Flag-Cdk7 fusion protein is listed in SEQ ID NO: 5

The gene encoding residues 2 (Tyrosine) to 323 (Leucine) of the human cyclin H gene was amplified by PCR in order to fuse the gene, in the correct translational reading frame, downstream of a Bab-epitope coding sequence on a vector pVL-1392-Bab. This baculovirus transfer vector is similar to pVL-1392-Flag except that it appends a Bab-epitope tag (Berkeley Antibody Co. AU-1 epitope) instead of a flag-epitope to a protein of interest. It is designed to append an epitope, for example, consisting of the amino acid sequence MDTYRYIRPAM (SEQ ID NO: 6), to the N-terminal of a protein encoded by a gene inserted at a Not 1 site on the vector. The PCR primers used for the amplification and modification of the cyclin H gene were: SEQ ID NO: 7, 5'-TAAC-CTGCGGCCGCCTACCACAACAGTAGTCAGAAGCGG and SEQ ID NO: 8, 5'-CGTTCTAGACGGTTAGAGAGAT-TCTACCAGGTC. The cyclin H PCR fragment was subcloned into pCR2.1 (Invitrogen), excised with restriction enzymes Not 1 (New England Biolabs) and Xba-1 (New England Biolabs), and inserted into the vector pVL-1392-Bab by DNA ligation. The Bab-Cyclin H coding sequence on the vector was confirmed via DNA sequencing and was presented in SEQ ID NO: 9. The deduced amino acid sequence of the Bab-Cyclin H fusion protein is listed in SEQ ID NO: 10

The epitope tagged gene, Flag-Cdk7 or Bab-Cyclin H was excised from the pVL epitope tagging vector via PstI/Kpn 1 digestion and inserted into the pFastBac expression vector for high level protein expression in insect cells using the Bac-to-Bac system (Gibco/Invitrogen). Baculovirus isolates were plaque purified using SF-900 serum free insect cells (Gibco) and clones producing high levels of the Flag-Cdk7 protein or Bab-Cyclin H protein were identified by western blot analysis of infected cell lysates using commercially available antibodies to Cdk7 or Cyclin H (Santa Cruz Biotechnology).

High titer stocks of baculoviruses encoding Flag-Cdk7 and Bab-Cyclin H were used to co-transfect insect cells, SF900 (Gibco). The co-infection was performed at a Multiplicity of Infection of 4 each and the cells were lysed 48 hours post infection. Expressions of the Flag-Cdk7 and Bab-Cyclin H in the co-transfected insect cells were confirmed by co-immunoprecipitation with anti-flag or anti-Bab antibodies, and western blotting of the proteins released from these immunoprecipitates. Co-immunoprecipitation results indicated that a anti-Flag antibody can precipitate a complex containing the Bab-Cyclin H protein and an anti-Bab antibody can precipitate a complex contain a Flag-Cdk7 protein.

The kinase activity of the CAK complex was confirmed by incubating 10 µg of the co-infected insect cell lysate in a buffer containing 50 mM Hepes pH 7.5, 10 mM $MgCl_2$, 1 mM DTT, 20 µM $NaoVO_4$, 0.2 mM PMSF, 25 µM ATP, 2 µCi $^{32}$P-ATP, and 1 µg of purified Flag-Cdk4 protein as a Cdk substrate at 30° C. for 1 hour. The results indicate that the Flag-cdk4 protein incorporated the $^{32}$P only when the CAK lysate was present, confirming the kinase activity of CAK. No incorporation was noted when GST, GST-Cyclin D1, or a GST-T loop protein were used as substrate, indicating the need for a substrate with more secondary structure than the 31 amino acids surrounding the T-loop Serine phosphorylation site affords.

Purification of a CAK Complex

The CAK complex was purified from co-infected SF-900 insect cells at 48 hours post infection by batch immunoaffinity purification. The infected cells were pelleted by centrifugation and lysed in 1/10 of the culture volume in a solution containing 50 mM Hepes pH 7.5, 10 mM $MgCl_2$, 1 mM DTT, 10 mM Beta-Glycerol phosphate, 20 uM Na-oVO4, 0.2 mM PMSF and 1 µg/mL each of leupeptin, aprotinin, and pepstatin on ice. Cells were mechanically lysed by trituration through a 22-gauge needle followed by sonication or alternately by nitrogen cavitation. The lysed cells were centrifuged at 50,000×G for 1 hour at 4° C. to remove debris and the supernatant was applied to 1/10 volume of prewashed Flag-M2 immunoaffinity resin (Sigma). The CAK complex, by nature of the Flag tagged Cdk7 protein, was allowed to bind to the Flag antibody of the resin overnight at 4° C. with gentle rocking. The resin was washed 4 times with 5 resin volumes of lysis buffer and the bound proteins were eluted by competition with 0.5 mg/mL Flag peptide (DYKDDDK, American Peptide Co, Inc., SEQ ID NO: 16) in a total of 2 resin volumes. To remove the Flag peptide, the eluted material was applied to PD-10 gel filtration columns (Pharmacia) under conditions recommended by the manufacturer.

The purified CAK complex contained within the PD-10 column fractions was confirmed and analyzed by SDS PAGE analysis followed by Coomassie-Blue staining. Quantitation was accomplished by SDS PAGE comparison to known quantities of BSA. SDS PAGE analysis confirmed that the estimated purity of the purified CAK complex was routinely better than 90%. It also demonstrated that the purified CAK complex comprises: 1) the Flag-Cdk7 protein with a molecular weight of approx. 40 KD; 2) the Bab-Cyclin H protein with a molecular weight of approx. 43 KD, and 3) a third protein with a molecular weight of approx. 51 KD, which is in similar stoicheometric amounts to that of Flag-Cdk7 and Bab-Cyclin H. Western blot analysis showed that the third protein was weakly immunoreactive to human MAT-1 specific antibody (Santa Cruz), suggesting that this protein is the insect cell MAT-1. This result is consistent with the observed CAK kinase activity in insect cells co-infected with genes encoding for Flag-Cdk7 and Bab-Cyclin H, in the absence of human MAT-1.

Cloning and Expression of a CAK Substrate

In order to develop an assay for the identification of CAK inhibitors that is amenable to high-throughput conditions, a CAK substrate that is easily produced in large quantities is needed.

The literature indicates that CAK phosphorylates the RNA polymerase II C-terminal domain (CTD) at the second serine residue of the CTD Tyr-Ser-Pro-Thr-Ser-Pro-Ser (SEQ ID NO: 11) repeat. This hepta-peptide sequence is repeated 52 times in the RNA polymerase II protein. A GST-CTD fusion protein comprising 3 repeats of this hepta-peptide sequence was designed and made in E. coli to serve as a high throughput substrate for CAK.

A first DNA molecule coding for the 3 repeats of this hepta-peptide sequence and a second DNA molecule that is complementary to the first DNA molecule were synthesized and inserted between the Bam H1 and Not 1 site of the E. coli expression vector pGEX 5×2. (Pharmacia). These two synthetic DNA molecules were:

```
                                       SEQ ID NO: 12
5'-GATCTATAGTCCCACATCACCGTCCGGATATAGTCCCACATCACCGT
CCTATAGTCCCACATCACCGTCCGC,
and, SEQ ID NO: 13
5'-GGCCGCGGACGGTGATGTGGGACTATAGGACGGTGATGTGGGACTAT
ATCCGGACGGTGATGTGGGACTATA.
```

The proper insertion on the obtained expression vector was confirmed by DNA sequencing. The DNA sequence encoding GST-CTD is presented in SEQ ID NO: 14. The deduced amino acid sequence of the GST-CTD fusion protein is listed in SEQ ID NO: 15.

An E. coli cell (BL21-DE3 pLys S) was transformed with the expression vector. The resulting E. coli host cell expressed high levels of a fusion protein consisting a Glutathione S-Transferase (GST) and the 3 repeats of the CTD under conditions recommended by the manufacturer (Pharmacia).

Purification of a CAK Substrate

The CAK substrate, GST-CTD was purified from E. coli cell (BL-21 DE3 pLys S strain) transformed with the expression vector for the fusion protein. The E. coli cells were grown to an $OD_{600}$ of 0.6. IPTG (Isopropyl thiogalactoside) was added at 1 mM final concentration to the cells to induce the expression of the fusion protein. After incubation with vigorous aeration for 3 to 4 hours, the induced E. coil cells were centrifuged at 10,000 RPM 4° C. for 15 minutes. The resulting bacterial pellet was resuspended in 1/20 volume of lysis buffer: 50 mM Tris pH 8.0, 150 mM NaCl, 1% NP-40, 1 mM DTT and 1 tablet/10 mL of protease inhibitors (Complete Mini, EDTA-free, Roche Diagnostics). GST-CTD was purified by batch affinity methods. The lysate was sonicated and centrifuged at 50,000×G for 30 minutes at 4° C. to remove insoluble material. The soluble fraction was applied to 1/100 culture volume of prewashed Glutathione Sepharose (Pharmacia) and allowed to bind for 3 hours at 4° C. with gentle rocking. The resin was washed 3 times with 10 volumes of lysis buffer and the bound material was eluted with 25 mM Glutathione in lysis buffer. Eluted material was extensively dialyzed against 50 mM Tris pH 8.0, 150 mM NaCl, 1 mM DTT, 0.2 mM PMSF. The approximately 29 kD GST-CTD protein was quantitated by comparison to known amounts of BSA by SDS PAGE followed by coomassie blue staining. The estimated purity of the purified GST-CTD protein was routinely better than 90%.

In Vitro Time-Resolved-Fluorescence Assay for the CAK Kinase Activity

Measurement of CAK kinase activity was accomplished using an antibody methodology in which a Europium labeled antibody binds preferentially to serine phosphorylated GST-CTD substrate. The long-lived europium label fluorescence allows a greater signal-to-noise ratio due to the delay in reading the emission wavelength, thereby eliminating signals from immediate fluorescence and fluorescent pharmaceutical screening compounds.

An appropriate anti Phospho-Serine antibody was first selected for the assay. Candidate anti Phospho-Serine antibodies were used to immunoprecipitate purified GST-CTD protein incubated under phosphorylating conditions with or without purified CAK. The immunoprecipitated GST-CTD protein was visualized by western blotting with anti-GST antibody. It was demonstrated that comparing to 4 other anti-phospho-serine antibodies tested, the 05-368 Anti-phospho-Ser/Thr-Pro, MPM-2 antibody (Upstate Biotechnology) immunoprecipitated the phosphorylated GST-CTD protein to a greater extent than non-phosphorylated GST-CTD. In addition, the 05-368 antibody did not appreciably immunoprecipitate Flag-Cdk7, which may interfere with experimental interpretation. Therefore, the 05-368 antibody was selected for the assay.

The time-resolved-fluorescence assay for the CAK kinase activity is performed as follows. In a well of a black glutathione coated 96 well micro titer plate (Pierce Chemical, No. 15360), the following reagents were added: 1) 25 ul substrate solution containing 500 ng purified GST-CTD in a buffer having 50 mM Hepes pH 7.5, 10 mM $MgCl_2$, 1 mM DTT, 0.2 mM PMSF, 40 uM Na-oVO4, and 22 uM ATP (as a background control, the buffer, including ATP but not substrate was added); 2) 2.5 ul of screening compounds in a diluent containing 30% DMSO/25 mM Hepes pH7.5 (As a control, the diluent only was added. Typically the final concentration of compound is 1 uM); and 3) 250 ng CAK enzyme complex in enzyme buffer containing 25 ul of 50 mM Hepes pH 7.5, 10 mM $MgCl_2$, 1 mM DTT, 0.2 mM PMSF, and 40 uM Na-oVO4. The micro titer plate was shaken for 2 minutes on a titer plate shaker and allowed to incubate at 30° C. for 20 minutes.

Subsequently, Kinase Stop Solution (75 mM EDTA, 0.2 mM PMSF, 1 mM DTT, 120 uM Na oVO4 in PBS) was added (50 ul/well). The plate was shaken for 2 minutes and incubated overnight at room temperature to allow substrate binding to the wells. The plate contents were flicked out, and the wells of the plate were washed 4 times with 350 ul of wash buffer (Delphia wash buffer, Perkin-Elmer, Inc.). The plate was tapped dry.

Antibody Solution containing 40 ng/well Europium labeled 05-368 antibody in Assay Buffer (Perkin-Elmer) was added (100 ul/well). The plate was shaken for 2 minutes and incubated for 1 hour at room temperature. The plate contents were flicked out, and the wells of the plate were washed 8 times with 350 ul of wash buffer (Delphia wash buffer, Perkin-Elmer, Inc.). The plate was tapped dry.

Delphia Enhancer Solution (Perkin-Elmer) was added (150 ul/well). The plate was shaken for 2 minutes and incubated for 1 hour at room temperature.

Fluorescence from each well was measured on an LJL Analyst (LJL Biosystems) using 360 nm excitation, 620 nm emission, and 400 nm dichroic filters with a set height of 2 mm using 100 flashes per well and a 200 μsec read delay.

Quantitative determinations of compound effectiveness in inhibiting CAK is made by comparing the background (no substrate) subtracted fluorescent counts of wells with diluent only with wells in which compounds were added. Similarly $IC_{50}$ curves can be generated with percent inhibition data using commercially available programs such as Prism (GraphPad Software Inc.).

A typical experiment will yield a signal to noise ratio of at least 8:1. A representative $IC_{50}$ determination curve is presented in FIG. 1. These data indicate that the CAK Time Resolved Fluorescence assay can be used to accurately compare inhibition $IC_{50}$ values over a wide range of concentrations. The assay allows the user to select compounds for further evaluation.

What is claimed is:

1. A compound selected from:

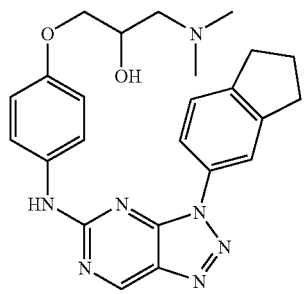

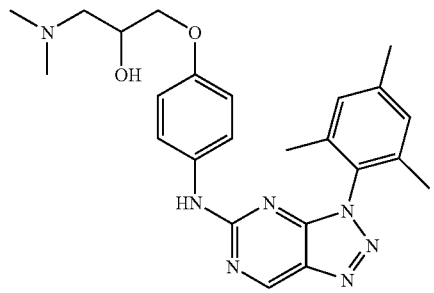

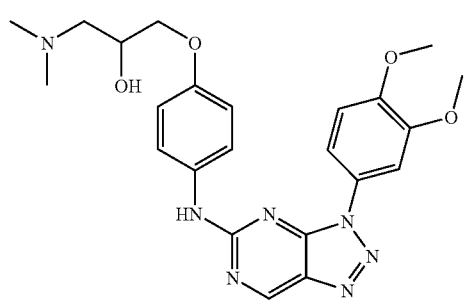

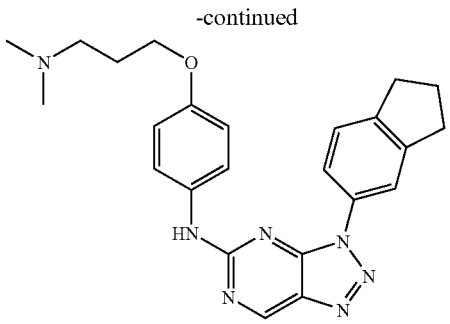

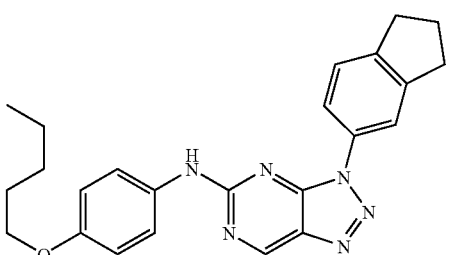

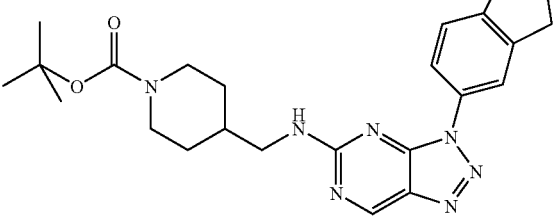

95
-continued
96
-continued
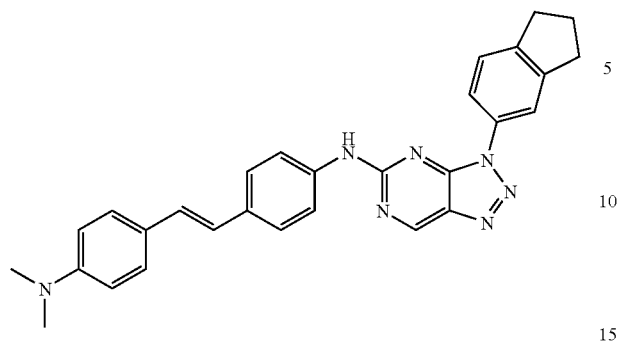
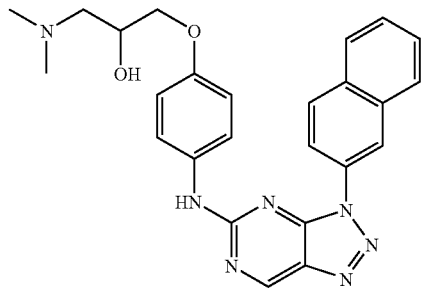
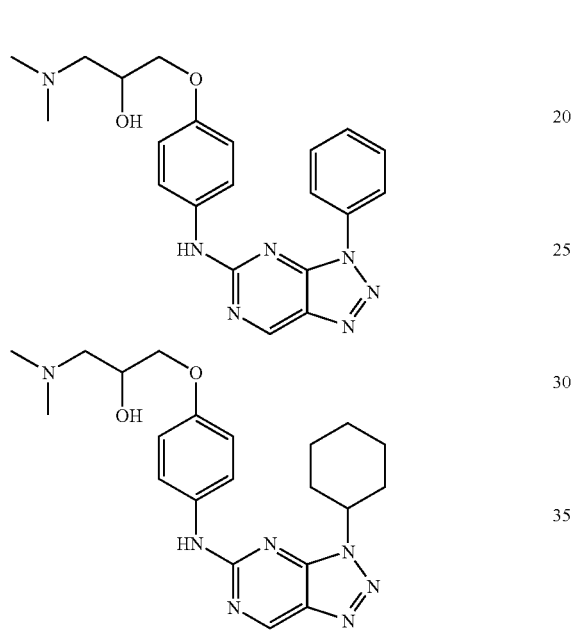
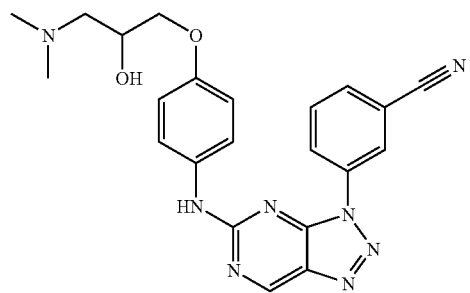
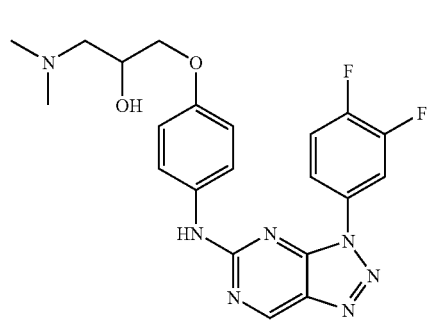

97
-continued
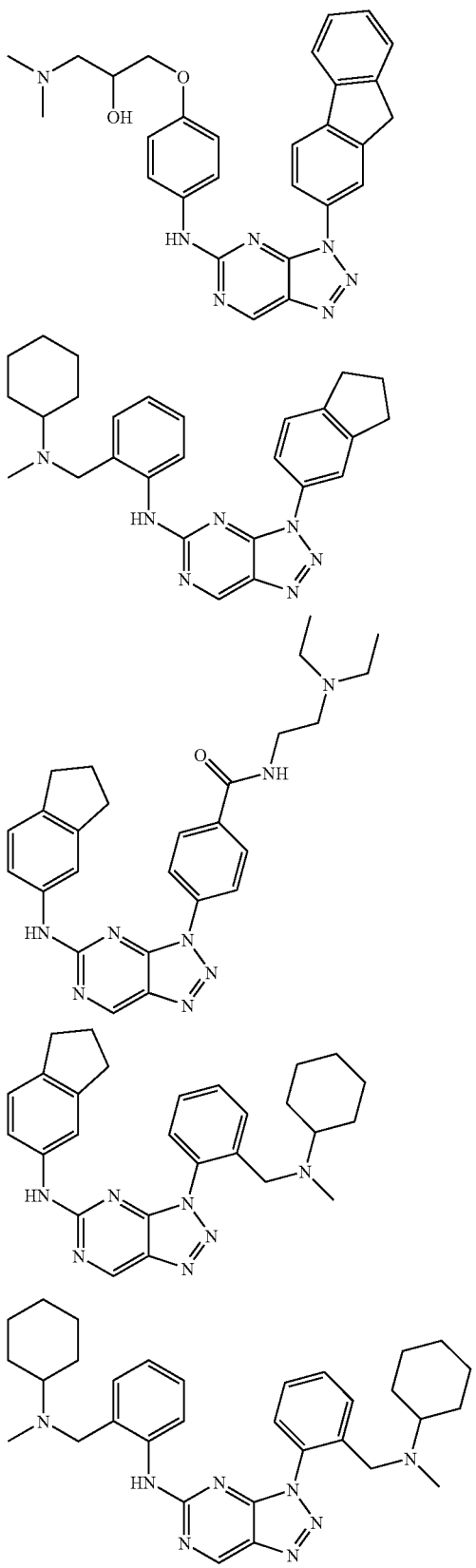
98
-continued
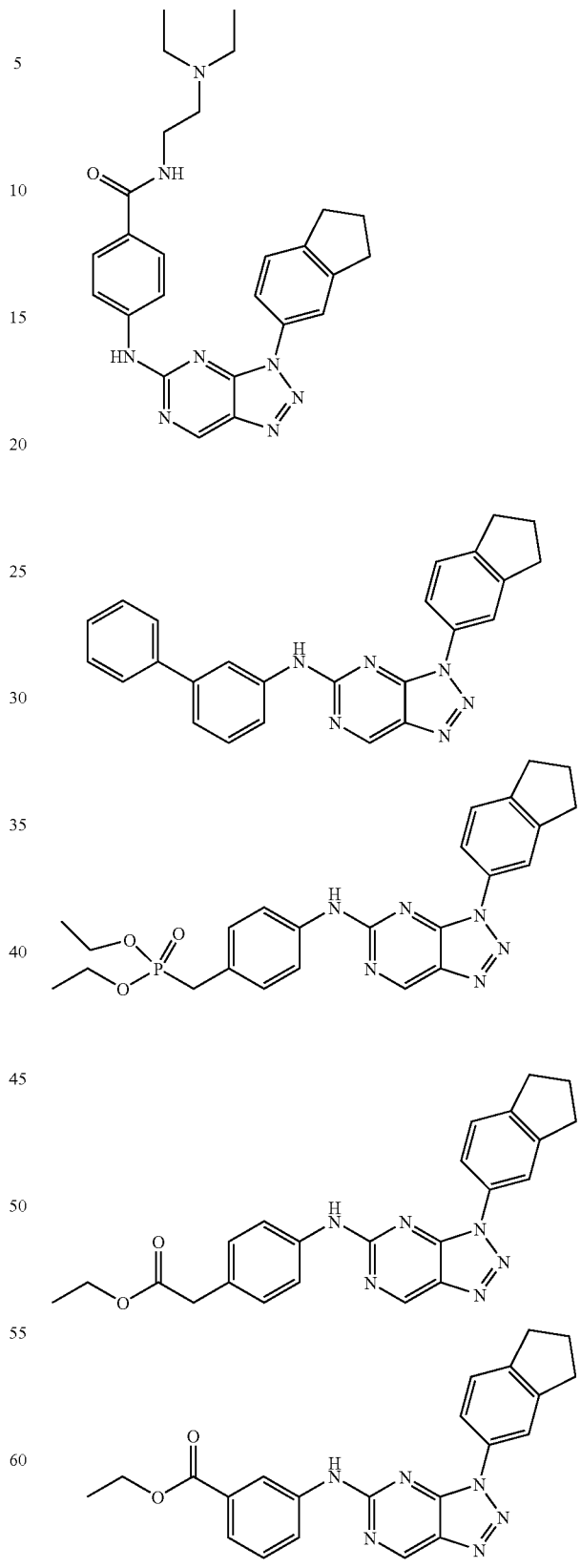

99 100
-continued -continued
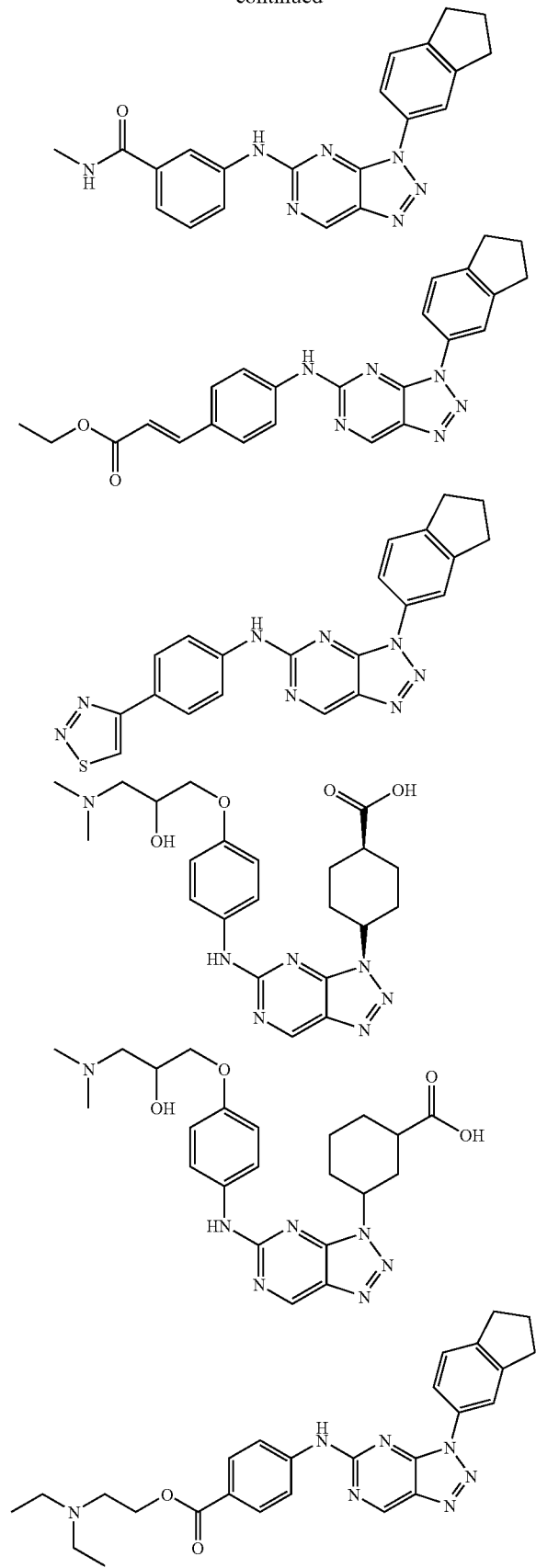

-continued
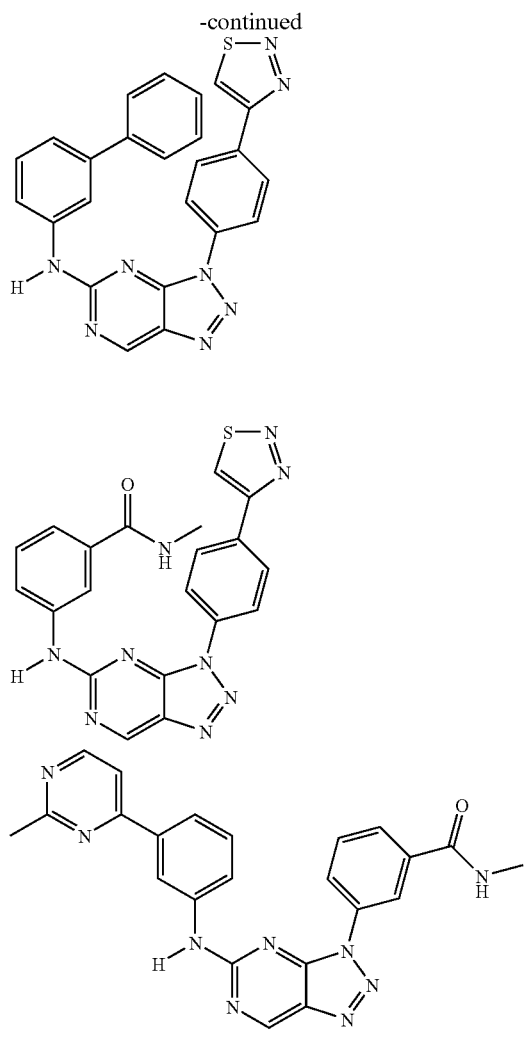
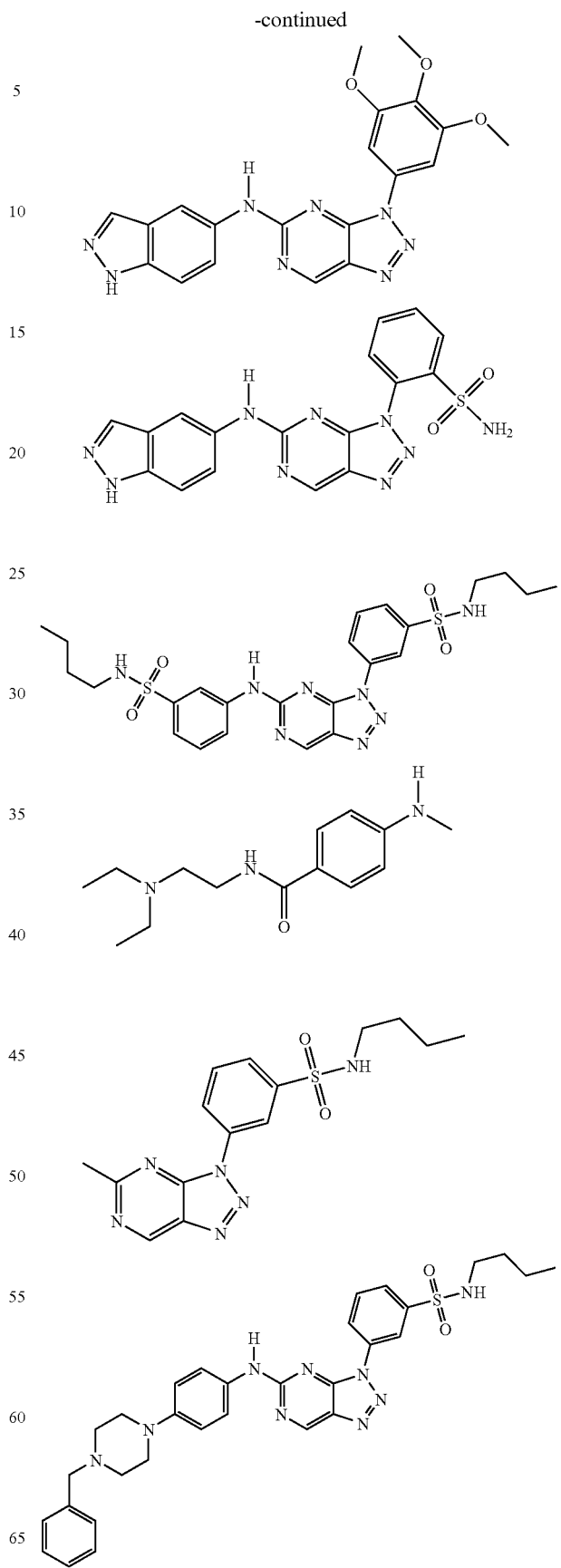

103
-continued
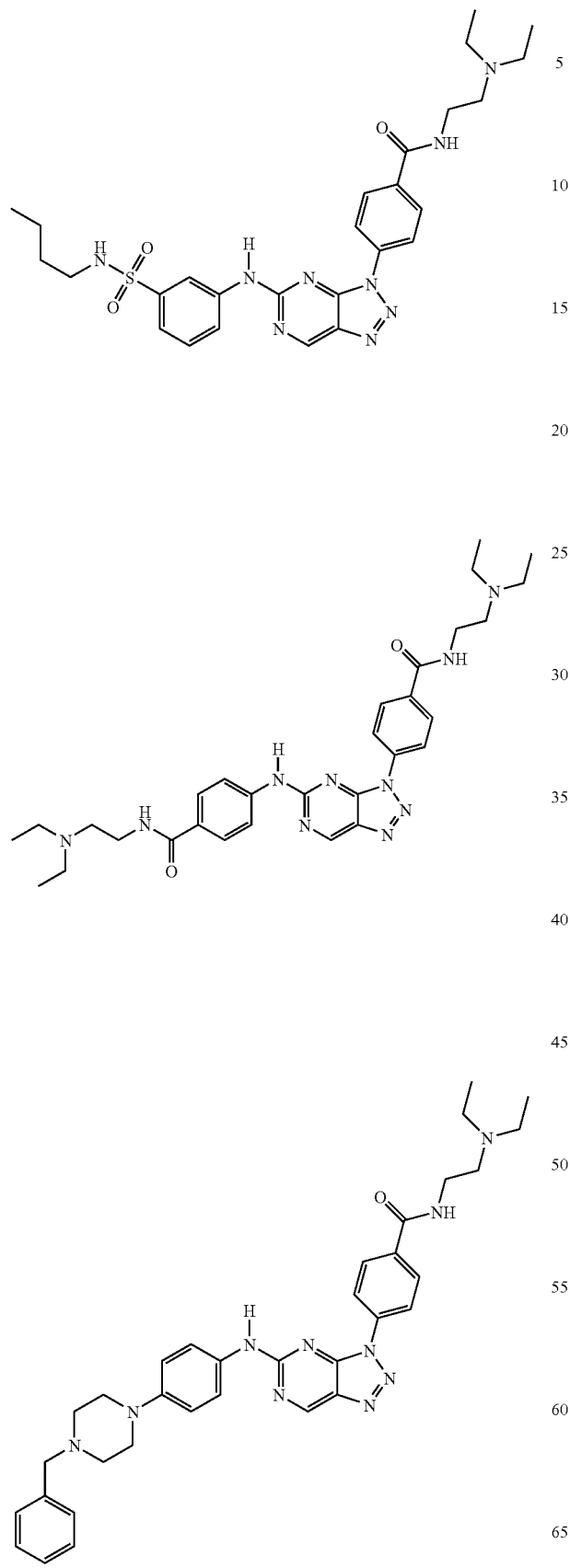
104
-continued
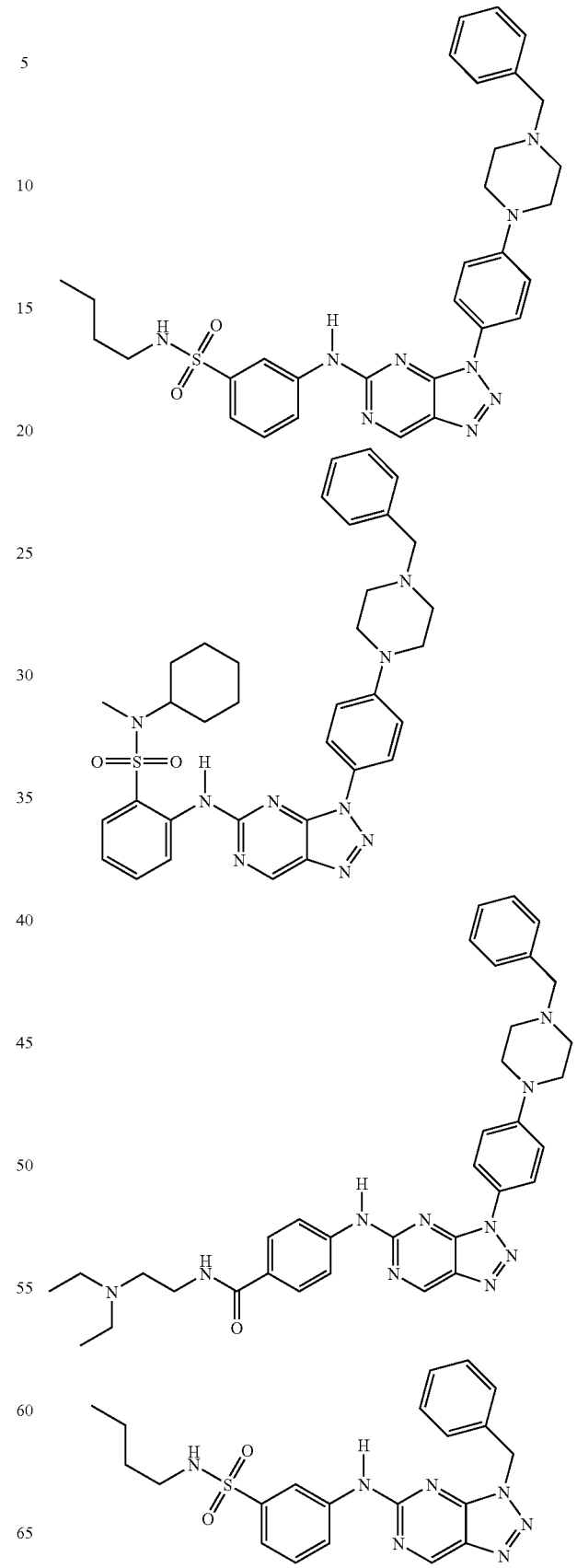

105
-continued
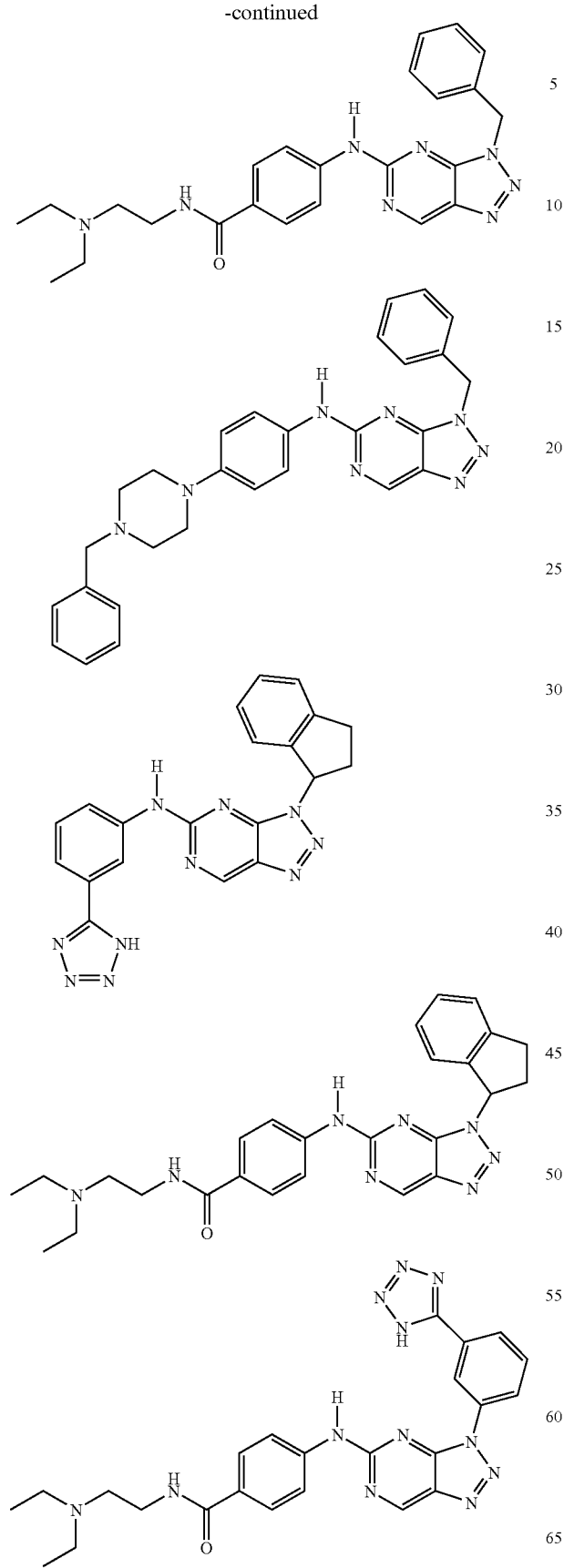
106
-continued
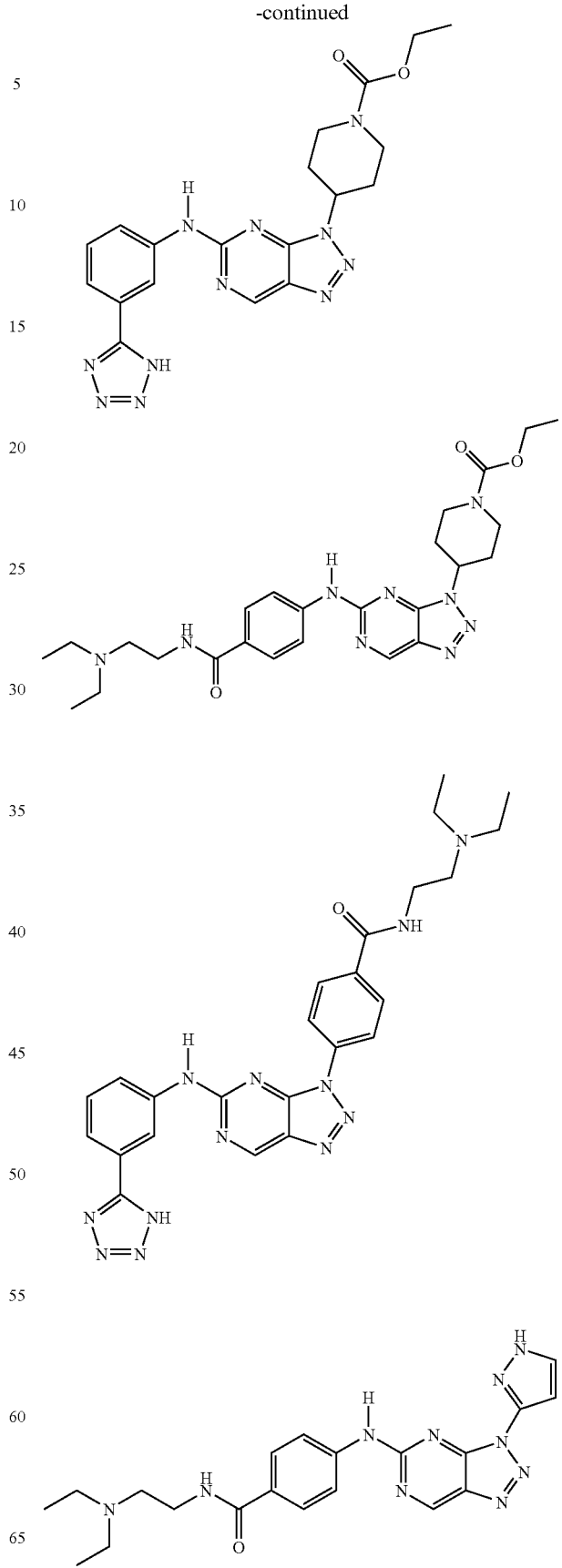

107 -continued
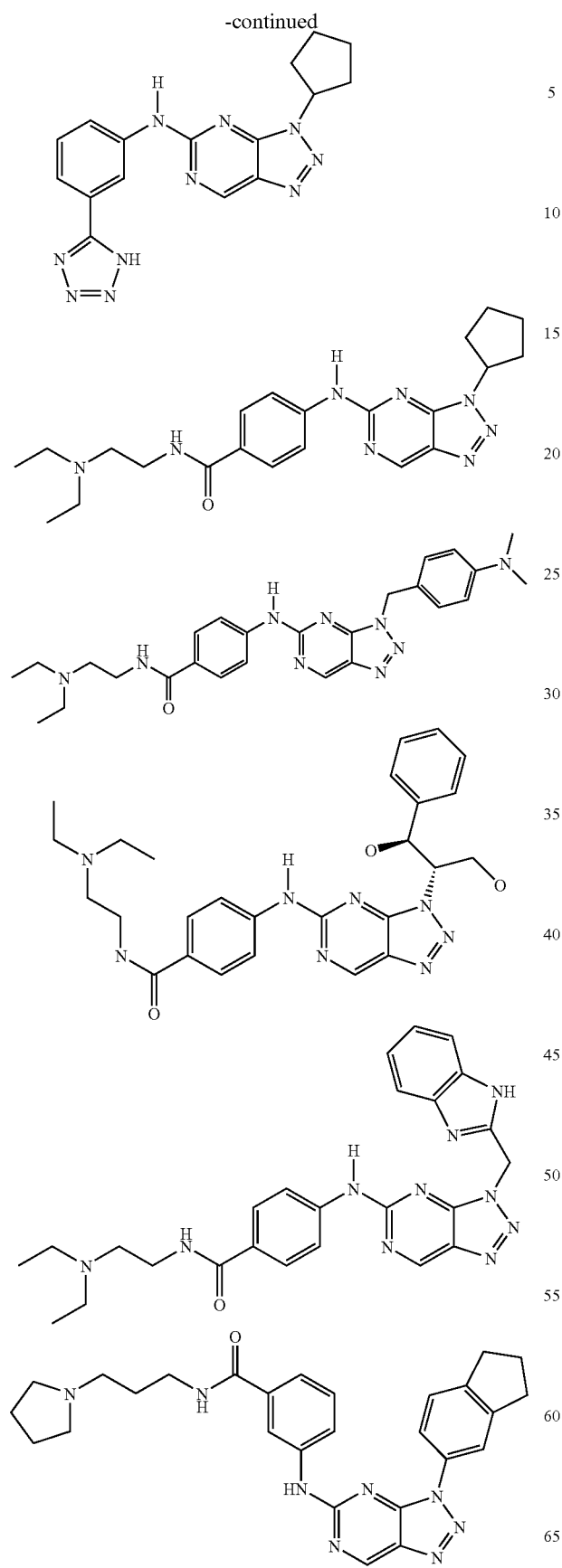
108 -continued
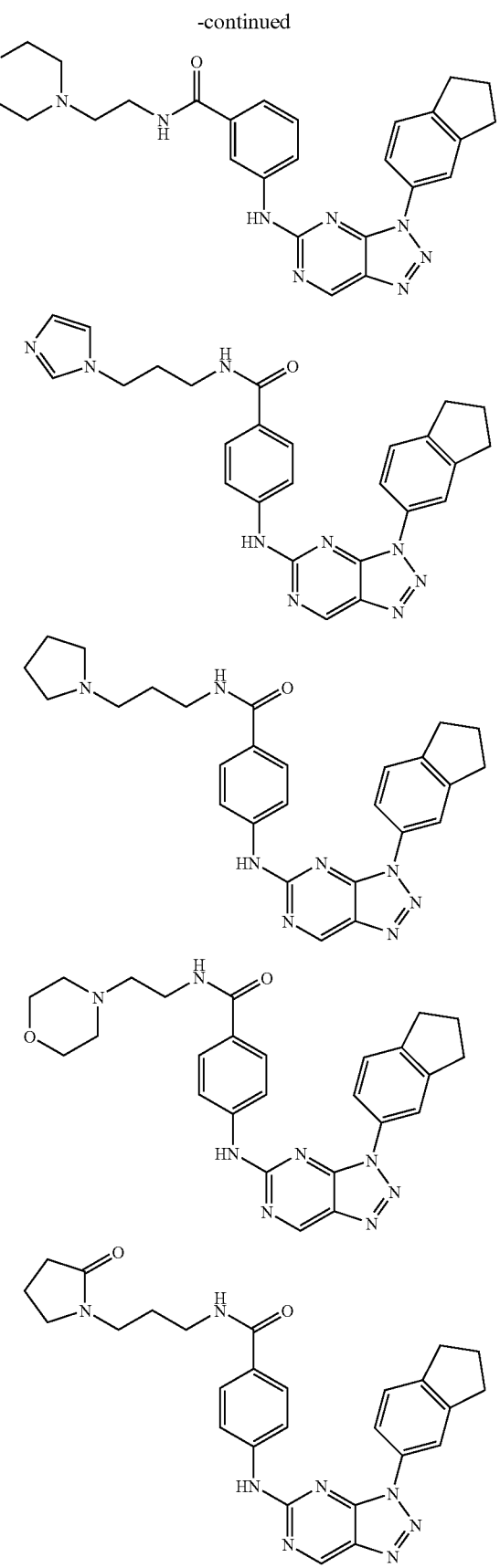

-continued
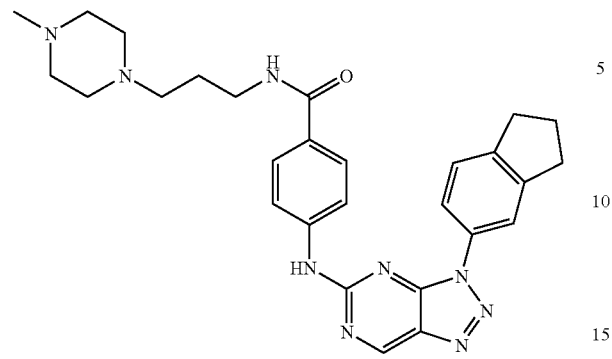

111
-continued
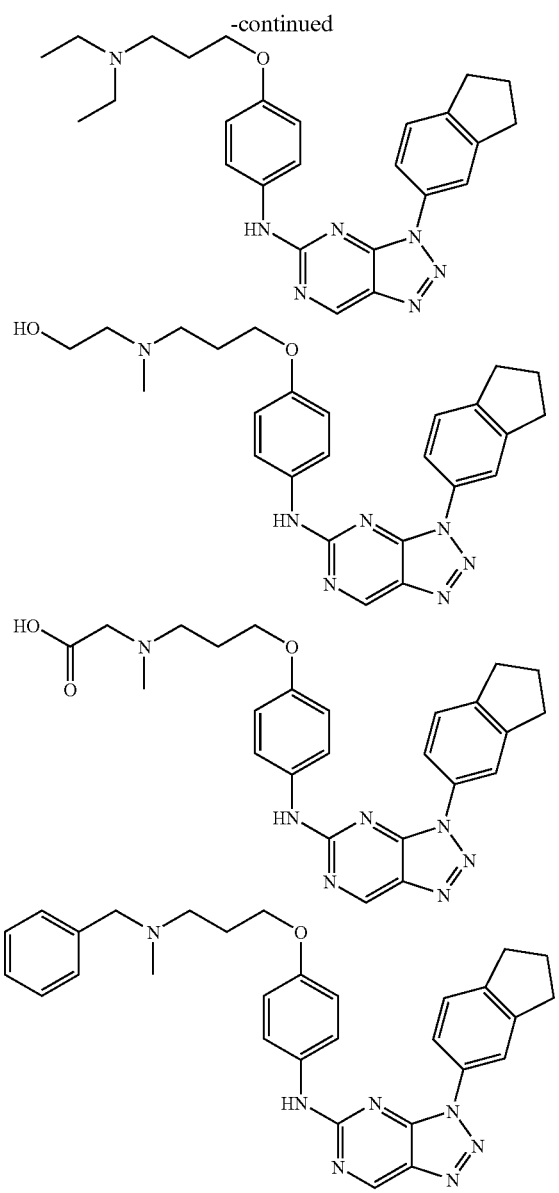
112
-continued
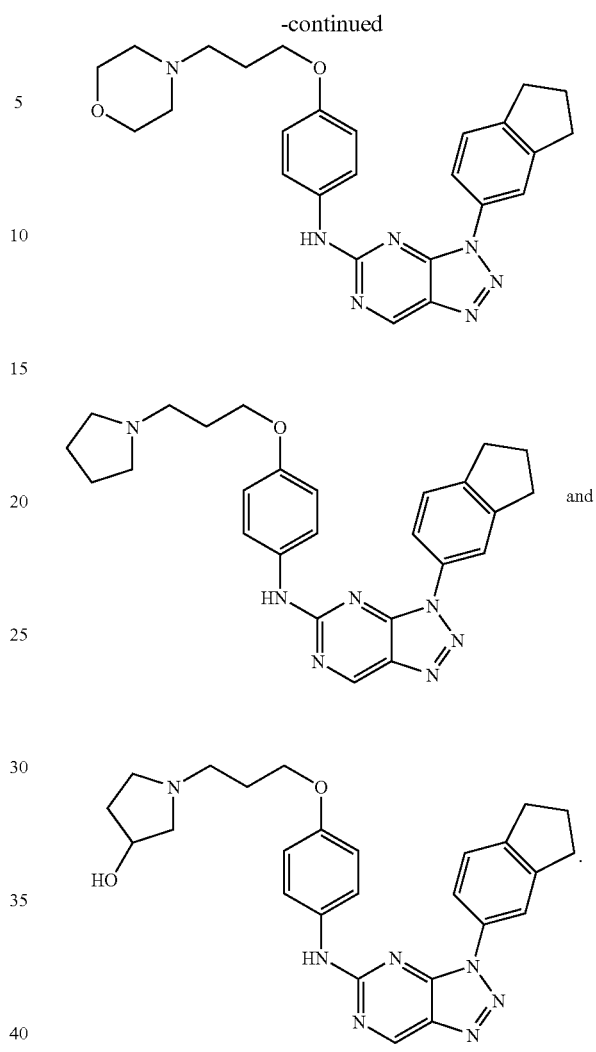
and
2. A pharmaceutical composition comprising a compound of claim 1 in a pharmaceutically acceptable carrier.
* * * * *

SEQUENCE LISTING

<160> NUMBER OF SEQ ID NOS: 16

Figure 1:
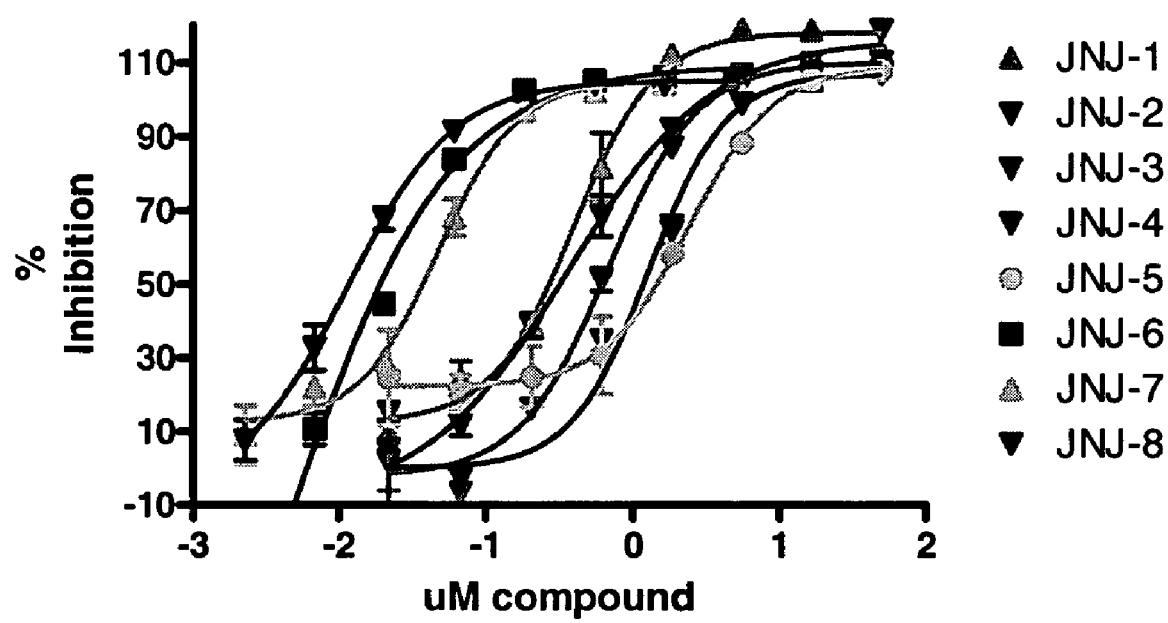
FIG. 1 illustrates the typical $IC_{50}$ determination by non-linear regression curve fit of several CAK inhibitors.

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      pLV-1392-FLAG Epitope

<400> SEQUENCE: 1

Met Asp Tyr Lys Asp Asp Asp Asp Lys Ala Ala
 1               5                   10

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttaaggcggc cgctctggac gtgaagtctc gg                                    32

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tttgaattct ctttaaaaaa ttagtttctt gggc                                  34

<210> SEQ ID NO 4
<211> LENGTH: 1071
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 4
atggactata aggacgacga tgacaaggcg gccgctctgg acgtgaagtc tcgggcaaag      60
cgttatgaga agctggactt ccttggggag ggacagtttg ccaccgttta caaggccaga     120
gataagaata ccaaccaaat tgtcgccatt aagaaaatca aacttggaca tagatcagaa     180
gctaaagatg gtataaatag aaccgcctta agagagataa aattattaca ggagctaagt    240

-continued

```
catccaaata taattggtct ccttgatgct tttggacata aatctaatat tagccttgtc    300
tttgatttta tggaaactga tctagaggtt ataataaagg ataatagtct tgtgctgaca    360
ccatcacaca tcaaagccta catgttgatg actcttcaag gattagaata tttacatcaa    420
cattggatcc tacataggga tctgaaacca aacaacttgt tgctagatga aaatggagtt    480
ctaaaactgg cagattttgg cctggccaaa tctttggga gccccaatag agcttataca     540
catcaggttg taaccaggtg gtatcgggcc cccgagttac tatttggagc taggatgtat    600
ggtgtaggtg tggacatgtg ggctgttggc tgtatattag cagagttact tctaagggtt    660 cctttttgc caggagattc agaccttgat cagctaacaa gaatatttga actttgggc     720 acaccaactg aggaacagtg gccggacatg tgtagtcttc cagattatgt gacatttaag    780 agttccctg gaatacctt gcatcacatc ttcagtgcag caggagacga cttactagat     840
ctcatacaag gcttattctt atttaatcca tgtgctcgaa ttacggccac acaggcactg    900
aaaatgaagt atttcagtaa tcggccaggg ccaacacctg gatgtcagct gccaagacca    960
aactgtccag tggaaacctt aaaggagcaa tcaaatccag ctttggcaat aaaaaggaaa   1020
agaacagagg cctagaaca aggaggattg cccaagaaac taatttttta a             1071
```

<210> SEQ ID NO 5
<211> LENGTH: 356
<212> TYPE: PRT
<213> ORGANISM: Artificial Sequence
<220> FEATURE:
<223> OTHER INFORMATION: Description of Artificial Sequence: Synthetic peptide construct

<400> SEQUENCE: 5

```
Met Asp Tyr Lys Asp Asp Asp Lys Ala Ala Leu Asp Val Lys
  1               5                  10                  15

Ser Arg Ala Lys Arg Tyr Glu Lys Leu Asp Phe Leu Gly Glu Gly Gln
                 20                  25                  30

Phe Ala Thr Val Tyr Lys Ala Arg Asp Lys Asn Thr Asn Gln Ile Val
             35                  40                  45

Ala Ile Lys Lys Ile Lys Leu Gly His Arg Ser Glu Ala Lys Asp Gly
         50                  55                  60

Ile Asn Arg Thr Ala Leu Arg Glu Ile Lys Leu Leu Gln Glu Leu Ser
 65                  70                  75                  80

His Pro Asn Ile Ile Gly Leu Leu Asp Ala Phe Gly His Lys Ser Asn
                 85                  90                  95

Ile Ser Leu Val Phe Asp Phe Met Glu Thr Asp Leu Glu Val Ile Ile
            100                 105                 110

Lys Asp Asn Ser Leu Val Leu Thr Pro Ser His Ile Lys Ala Tyr Met
        115                 120                 125

Leu Met Thr Leu Gln Gly Leu Glu Tyr Leu His Gln His Trp Ile Leu
    130                 135                 140

His Arg Asp Leu Lys Pro Asn Asn Leu Leu Asp Glu Asn Gly Val
145                 150                 155                 160

Leu Lys Leu Ala Asp Phe Gly Leu Ala Lys Ser Phe Gly Ser Pro Asn
                165                 170                 175

Arg Ala Tyr Thr His Gln Val Val Thr Arg Trp Tyr Arg Ala Pro Glu
            180                 185                 190

Leu Leu Phe Gly Ala Arg Met Tyr Gly Val Gly Val Asp Met Trp Ala
        195                 200                 205

Val Gly Cys Ile Leu Ala Glu Leu Leu Leu Arg Val Pro Phe Leu Pro
```

```
            210                 215                 220
Gly Asp Ser Asp Leu Asp Gln Leu Thr Arg Ile Phe Glu Thr Leu Gly
225                 230                 235                 240

Thr Pro Thr Glu Glu Gln Trp Pro Asp Met Cys Ser Leu Pro Asp Tyr
                245                 250                 255

Val Thr Phe Lys Ser Phe Pro Gly Ile Pro Leu His His Ile Phe Ser
            260                 265                 270

Ala Ala Gly Asp Asp Leu Leu Asp Leu Ile Gln Gly Leu Phe Leu Phe
        275                 280                 285

Asn Pro Cys Ala Arg Ile Thr Ala Thr Gln Ala Leu Lys Met Lys Tyr
290                 295                 300

Phe Ser Asn Arg Pro Gly Pro Thr Pro Gly Cys Gln Leu Pro Arg Pro
305                 310                 315                 320

Asn Cys Pro Val Glu Thr Leu Lys Glu Gln Ser Asn Pro Ala Leu Ala
                325                 330                 335

Ile Lys Arg Lys Arg Thr Glu Ala Leu Glu Gln Gly Gly Leu Pro Lys
            340                 345                 350

Lys Leu Ile Phe
        355

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      pVL-1392-Bab Epitope

<400> SEQUENCE: 6

Met Asp Thr Tyr Arg Tyr Ile Arg Pro Ala Ala Ala
  1               5                  10

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
taacctgcgg ccgcctacca caacagtagt cagaagcgg                              39

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cgttctagac ggttagagag attctaccag gtc                                    33

<210> SEQ ID NO 9
<211> LENGTH: 1005
<212> TYPE: DNA
<213> ORGANISM: Artificial Sequence
<220> FEATURE:
<223> OTHER INFORMATION: Description of Artificial Sequence: Synthetic
      nucleotide construct

<400> SEQUENCE: 9
```

-continued

```
atggacacct atcggtatat acgtcctgcg gccgcctacc acaacagtag tcagaagcgg      60
cactggacct tctccagcga ggagcagctg gcaagactgc gggctgacgc caaccgcaaa     120
ttcagatgca aagccgtggc caacggaag gttcttccga atgatccagt ctttcttgag      180
cctcatgaag aaatgacact ctgcaaatac tatgagaaaa ggttattgga attctgttcg    240
gtgtttaagc cagcaatgcc aagatctgtt gtgggtacgg cttgtatgta tttcaaacgt    300
ttttatctta ataactcagt aatggaatat caccccagga taataatgct cacttgtgca    360
tttttggcct gcaaagtaga tgaattcaat gtatctagtc ctcagtttgt tggaaacctc    420
cgggagagtc ctcttggaca ggagaaggca cttgaacaga tactggaata tgaactactt    480
cttatacagc aacttaattt ccaccttatt gtccacaatc cttacagacc atttgagggc    540
ttcctcatcg acttaaagac ccgctatccc atattggaga tccagagat tttgaggaaa     600 acagctgatg actttcttaa tagaattgca ttgacggatg cttacctttt atacacacct    660
tcccaaattg ccctgactgc catttttatct agtgcctcca gggctggaat tactatggaa    720
agttatttat cagagagtct gatgctgaaa gagaacagaa cttgcctgtc acagttacta    780
gatataatga aaagcatgag aaacttagta agaagtatg aaccacccag atctgaagaa     840
gttgctgttc tgaaacagaa gttggagcga tgtcattctg ctgagcttgc acttaacgta    900
atcacgaaga agaggaaagg ctatgaagat gatgattacg tctcaaagaa atccaaacat    960
gaggaggaag aatggactga tgacgacctg gtagaatctc tctaa                   1005
```

<210> SEQ ID NO 10
<211> LENGTH: 334
<212> TYPE: PRT
<213> ORGANISM: Artificial Sequence
<220> FEATURE:
<223> OTHER INFORMATION: Description of Artificial Sequence: Synthetic peptide construct

<400> SEQUENCE: 10

```
Met Asp Thr Tyr Arg Tyr Ile Arg Pro Ala Ala Tyr His Asn Ser
 1               5                  10                  15

Ser Gln Lys Arg His Trp Thr Phe Ser Ser Glu Glu Gln Leu Ala Arg
            20                  25                  30

Leu Arg Ala Asp Ala Asn Arg Lys Phe Arg Cys Lys Ala Val Ala Asn
        35                  40                  45

Gly Lys Val Leu Pro Asn Asp Pro Val Phe Leu Glu Pro His Glu Glu
    50                  55                  60

Met Thr Leu Cys Lys Tyr Tyr Glu Lys Arg Leu Leu Glu Phe Cys Ser
65                  70                  75                  80

Val Phe Lys Pro Ala Met Pro Arg Ser Val Val Gly Thr Ala Cys Met
                85                  90                  95

Tyr Phe Lys Arg Phe Tyr Leu Asn Asn Ser Val Met Glu Tyr His Pro
            100                 105                 110

Arg Ile Ile Met Leu Thr Cys Ala Phe Leu Ala Cys Lys Val Asp Glu
        115                 120                 125

Phe Asn Val Ser Ser Pro Gln Phe Val Gly Asn Leu Arg Glu Ser Pro
    130                 135                 140

Leu Gly Gln Glu Lys Ala Leu Glu Gln Ile Leu Glu Tyr Glu Leu Leu
145                 150                 155                 160

Leu Ile Gln Gln Leu Asn Phe His Leu Ile Val His Asn Pro Tyr Arg
                165                 170                 175
```

```
Pro Phe Glu Gly Phe Leu Ile Asp Leu Lys Thr Arg Tyr Pro Ile Leu
            180                 185                 190

Glu Asn Pro Glu Ile Leu Arg Lys Thr Ala Asp Asp Phe Leu Asn Arg
        195                 200                 205

Ile Ala Leu Thr Asp Ala Tyr Leu Leu Tyr Thr Pro Ser Gln Ile Ala
    210                 215                 220

Leu Thr Ala Ile Leu Ser Ser Ala Ser Arg Ala Gly Ile Thr Met Glu
225                 230                 235                 240

Ser Tyr Leu Ser Glu Ser Leu Met Leu Lys Glu Asn Arg Thr Cys Leu
                245                 250                 255

Ser Gln Leu Leu Asp Ile Met Lys Ser Met Arg Asn Leu Val Lys Lys
            260                 265                 270

Tyr Glu Pro Pro Arg Ser Glu Glu Val Ala Val Leu Lys Gln Lys Leu
        275                 280                 285

Glu Arg Cys His Ser Ala Glu Leu Ala Leu Asn Val Ile Thr Lys Lys
    290                 295                 300

Arg Lys Gly Tyr Glu Asp Asp Tyr Val Ser Lys Lys Ser Lys His
305                 310                 315                 320

Glu Glu Glu Glu Trp Thr Asp Asp Leu Val Glu Ser Leu
                325                 330

<210> SEQ ID NO 11
<211> LENGTH: 7
<212> TYPE: PRT
<213> ORGANISM: Unknown Organism
<220> FEATURE:
<223> OTHER INFORMATION: Description of Unknown Sequence: Unknown
      RNAP CTD peptide

<400> SEQUENCE: 11

Tyr Ser Pro Thr Ser Pro Ser
 1               5

<210> SEQ ID NO 12
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gatctatagt cccacatcac cgtccggata tagtcccaca tcaccgtcct atagtcccac      60
atcaccgtcc gc                                                         72

<210> SEQ ID NO 13
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ggccgcggac ggtgatgtgg gactatagga cggtgatgtg ggactatatc cggacggtga      60
tgtgggacta ta                                                         72

<210> SEQ ID NO 14
<211> LENGTH: 762
<212> TYPE: DNA
<213> ORGANISM: Artificial Sequence
```

<220> FEATURE:
<223> OTHER INFORMATION: Description of Artificial Sequence: Synthetic nucleotide construct

<400> SEQUENCE: 14

```
atgtcccta tactaggtta ttggaaaatt aagggccttg tgcaacccac tcgacttctt    60
ttggaatatc ttgaagaaaa atatgaagag catttgtatg agcgcgatga aggtgataaa   120
tggcgaaaca aaaagtttga attgggtttg gagtttccca atcttcctta ttatattgat   180
ggtgatgtta aattaacaca gtctatggcc atcatacgtt atatagctga caagcacaac   240
atgttgggtg gttgtccaaa agagcgtgca gagatttcaa tgcttgaagg agcggttttg   300
gatattagat acggtgtttc gagaattgca tatagtaaag actttgaaac tctcaaagtt   360
gattttctta gcaagctacc tgaaatgctg aaaatgttcg aagatcgttt atgtcataaa   420
acatatttaa atggtgatca tgtaacccat cctgacttca tgttgtatga cgctcttgat   480
gttgttttat acatggaccc aatgtgcctg gatgcgttcc caaaattagt ttgttttaaa   540
aaacgtattg aagctatccc acaaattgat aagtacttga atccagcaa gtatatagca   600
tggcctttgc agggctggca agccacgttt ggtggtggcg accatcctcc aaaatcggat   660
ctgatcgaag tcgtgggat ctatagtccc acatcaccgt ccggatatag tcccacatca   720
ccgtcctata gtcccacatc accgtccgcg gccgcatcgt ga                      762
```

<210> SEQ ID NO 15
<211> LENGTH: 253
<212> TYPE: PRT
<213> ORGANISM: Artificial Sequence
<220> FEATURE:
<223> OTHER INFORMATION: Description of Artificial Sequence: Synthetic peptide construct

<400> SEQUENCE: 15

```
Met Ser Pro Ile Leu Gly Tyr Trp Lys Ile Lys Gly Leu Val Gln Pro
  1               5                  10                  15

Thr Arg Leu Leu Leu Glu Tyr Leu Glu Glu Lys Tyr Glu Glu His Leu
             20                  25                  30

Tyr Glu Arg Asp Glu Gly Asp Lys Trp Arg Asn Lys Lys Phe Glu Leu
         35                  40                  45

Gly Leu Glu Phe Pro Asn Leu Pro Tyr Tyr Ile Asp Gly Asp Val Lys
     50                  55                  60

Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190
```

```
Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Ile Glu Gly
        210                 215                 220

Arg Gly Ile Tyr Ser Pro Thr Ser Pro Ser Gly Tyr Ser Pro Thr Ser
225                 230                 235                 240

Pro Ser Tyr Ser Pro Thr Ser Pro Ser Ala Ala Ala Ser
                245                 250

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      FLAG peptide

<400> SEQUENCE: 16

Asp Tyr Lys Asp Asp Asp Lys
  1               5
```